(12) United States Patent
An et al.

(10) Patent No.: US 10,266,900 B2
(45) Date of Patent: Apr. 23, 2019

(54) METHOD FOR DETECTING PRECANCEROUS LESIONS

(71) Applicant: GENOMICTREE, INC., Daejeon (KR)

(72) Inventors: Sungwhan An, Daejeon (KR); Tae Jeong Oh, Daejeon (KR)

(73) Assignee: GENOMICTREE, INC., Daejeon (KR)

( * ) Notice: Subject to any disclaimer, the term of this patent is extended or adjusted under 35 U.S.C. 154(b) by 13 days.

(21) Appl. No.: 14/900,149

(22) PCT Filed: Aug. 14, 2014

(86) PCT No.: PCT/KR2014/007582
§ 371 (c)(1),
(2) Date: Dec. 19, 2015

(87) PCT Pub. No.: WO2015/023146
PCT Pub. Date: Feb. 19, 2015

(65) Prior Publication Data
US 2016/0153050 A1    Jun. 2, 2016

(30) Foreign Application Priority Data

Aug. 14, 2013 (KR) ........................ 10-2013-0096524

(51) Int. Cl.
*C12Q 1/6886* (2018.01)
*C07H 21/04* (2006.01)
*C12Q 1/68* (2018.01)

(52) U.S. Cl.
CPC ...... *C12Q 1/6886* (2013.01); *C12Q 2600/112* (2013.01); *C12Q 2600/118* (2013.01); *C12Q 2600/154* (2013.01)

(58) Field of Classification Search
None
See application file for complete search history.

(56) References Cited

U.S. PATENT DOCUMENTS

| 2012/0264640 A1* | 10/2012 | An | C12Q 1/686 506/9 |
| 2016/0040244 A1* | 2/2016 | An | C12O 1/6886 506/2 |

FOREIGN PATENT DOCUMENTS

| CN | 101970692 A | 2/2011 | |
| CN | 102686744 A | 9/2012 | |
| KR | 10-2011-0049430 A | 5/2011 | |
| KR | 10-1142131 B1 | 5/2012 | |
| WO | WO-2011055916 A2 * | 5/2011 | ............. C12Q 1/686 |

OTHER PUBLICATIONS

Matsusaka et al. (Cancer Res. vol. 71, No. 23, , pp. 7187-7197, 2011 (Year: 2011).*
Hoehn et al. (Cancer Res,vol. 72, p. 4517, Apr. 12, 2012). (Year: 2012).*
Oh et al. (The J. of Molecular Diagnostics, vol. 15, No. 4, pp. 498-507, Jun. 12, 2013). (Year: 2013).*
Alquist, D., et al., "Colorectal Cancer Screening by Detection of Altered Human DNA in Stool: Feasibility of a Multitarget Assay Panel", Gastroenterology, Nov. 2000, pp. 1219-1227, vol. 119, No. 5.
Chen, X., et al., "Detecting Tumor-related Alterations in Plasma or Serum DNA of Patients Diagnosed with Breast Cancer", Clinical Cancer Research, Sep. 1999, pp. 2297-2303, vol. 5.
Devos, T., et al., "Circulating Methylated SEPT9 DNA in Plasma Is a Biomarker for Colorectal Cancer", Clinical Chemistry, Jul. 2009, pp. 1337-1346, vol. 55, No. 7.
Esteller, M., et al., "Detection of Aberrant Promoter Hypermethylation of Tumor Suppressor Genes in Serum DNA from Non-Small Cell Lung Cancer Patients", Cancer Research, Jan. 1, 1999, pp. 67-70, vol. 59.
Kane, M., et al., "Methylation of the hMLH1 Promoter Correlates with Lack of Expression of hMLH1 in Sporadic Colon Tumors and Mismatch Repair-defective Human Tumor Cell Lines", Cancer Research, Mar. 1, 1997, pp. 808-811, vol. 57.
Kim, Y., et al., "Decreased syndecan-2 expression correlates with trichostatin-A induced-morphological changes and reduced tumorigenic activity in colon carcinoma cells", Oncogene, Feb. 13, 2003, pp. 826-830, vol. 22, No. 6.
Kopreski, M., et al., "Detection of Tumor Messenger RNA in the Serum of Patients with Malignant Melanoma", Clinical Cancer Research, Aug. 1999, pp. 1961-1965, vol. 5.
Lee, H., et al., "Syndecan-2 cytoplasmic domain regulates colon cancer cell migration via interaction with syntenin-1", Biochemical and Biophysical Research Communications, May 27, 2011, pp. 148-153, vol. 409, No. 1.
Marzese, D., et al., "Diagnostic andn prognostic value of circulating tumor-related DNA in cancer patients", Expert Review of Molecular Diagnostics, Nov. 2013, pp. 827-844, vol. 13, No. 8.
Messaoudi, S., et al., "Circulating cell free DNA: Preanalytical considerations", Clinica Chimica Acta, Sep. 23, 2013, pp. 222-230, vol. 424.
Miyashiro, I., et al., "Molecular Strategy for Detecting Metastatic Cancers with Use of Multiple Tumor-specific MAGE-A Genes", Clinical Chemistry, Mar. 2001, pp. 505-512, vol. 47, No. 3.

(Continued)

*Primary Examiner* — Jeanine A Goldberg
(74) *Attorney, Agent, or Firm* — Hultquist, PLLC; Steven J. Hultquist

(57) ABSTRACT

The present invention relates to the novel use of syndecan-2 (SDC2) gene as a CpG methylation biomarker for detecting precancerous lesions, and more particularly, to the use of the SDC2 gene as a biomarker to early diagnose colorectal precancerous lesions by measuring the degree of methylation of the SDC2 gene. The present invention provides a method of providing information for diagnosis of precancerous lesions by detecting methylation of the CpG islands of the SDC2 gene. In addition, the use of the methylation detection and kit according to the present invention makes it possible to diagnose colorectal precancerous lesions at an early transformation stage, thus enabling the early diagnosis of colorectal precancerous lesions. Furthermore, the methylation detection method and kit of the present invention enables colorectal precancerous lesions to be effectively diagnosed in an accurate and rapid manner compared to conventional methods.

4 Claims, 5 Drawing Sheets
Specification includes a Sequence Listing.

(56) References Cited

OTHER PUBLICATIONS

Oh, T., et al., "Genome-Wide Identification and Validation of a Novel Methylation Biomarker, SDC2, for Blood-Based Detection of Colorectal Cancer", The Journal of Molecular Diagnostics, Jul. 2013, pp. 498-507, vol. 15, No. 4.
Palmisano, W., et al., "Predicting Lung Cancer by Detecting Aberrant Promoter Methylation in Sputum", Cancer Research, Nov. 1, 2000, pp. 5954-5958, vol. 60.
Park, H., et al., "Syndecan-2 Mediates Adhesion and Proliferation of Colon Carcinoma Cells", The Journal of Biological Chemistry, Aug. 16, 2002, pp. 29730-29736, vol. 277, No. 33.
Potter, N., et al., "Validation of a Real-Time PCR-Based Qualitative Assay for the Detection of Methylated SEPT9 DNA in Human Plasma", Clinical Chemistry, Sep. 2014, pp. 1183-1191, vol. 60, No. 9.
Sanchez-Cespedes, M., et al., "Gene Promoter Hypermethylation in Tumors and Serum of Head and Neck Cancer Patients", Cancer Research, Feb. 15, 2000, pp. 892-895, vol. 60.
Sozzi, G., et al., "Detection of Microsatellite Alterations in Plasma DNA of Non-Small Cell Lung Cancer Patients: A Prospect for Early Diagnosis", Clinical Cancer Research, Oct. 1999, pp. 2689-2692, vol. 5.
Sueoka, E., et al., "Heterogeneous Nuclear Ribonucleoprotein B1 as a New Marker of Early Detection for Human Lung Cancers", Cancer Research, Apr. 1, 1999, pp. 1404-1407, vol. 59.
Vicente, C., et al., "Syndecan-2 upregulated in colorectal cancer cells through interactions with extracellular matrix produced by stromal fibroblasts", BMC Cell Biology, May 25, 2013, pp. 1-14, vol. 14, No. 25.
Cross, S., et al., "CpG islands and genes", "Current Opinion in Genetics and Development", Jun. 1995, pp. 309-314, vol. 5, No. 3.

\* cited by examiner colorectal cancer cell line colorectal tissue methylation level

- N: normal colorectal tissue
- HP: Hyperplastic polyps
- Ad: Adenomatous polyps ROC curve analysis

- AUC = 0.971 (95% CI, 0.885-0.996)
- Cut-off > 4.03
- P = 0.0001
- sensitivity = 95.9% (95% CI, 86.0%-99.4%)
- specificity = 100% (95% CI, 48.0%-100%)

methylation level

ROC curve analysis methylation level

N.D: Not detected

- N: Normal Control
- HP: Hyperplastic polyp
- Ad: Adenomatous polyp
- CRC: Colorectal cancer ROC curve analysis methylation level ROC curve analysis

METHOD FOR DETECTING PRECANCEROUS LESIONS

CROSS-REFERENCE TO RELATED APPLICATIONS

This application is a U.S. national phase under the provisions of 35 U.S.C. § 371 of International Patent Application No. PCT/KR2014/007582 filed Aug. 14, 2014, which in turn claims priority of Korean Patent Application No. 10-2013-0096524 filed Aug. 14, 2013. The disclosures of such international patent application and Korean priority patent application are hereby incorporated herein by reference in their respective entireties, for all purposes.

TECHNICAL FIELD

The present invention relates to the use of syndecan-2 (SDC2) gene as a CpG methylation biomarker which is used to detect precancerous lesions, which correspond to a cell proliferative disorder of colorectal tissue, based on an aberrant methylation event that occurs in a specific gene region when normal cells transform into hyperplastic cells. More particularly, the present invention relates to a method of early detecting precancerous lesions by measuring the degree of methylation of a specific region of the SDC2 gene.

BACKGROUND ART

Even at the present time when medical science has advanced, the 5-year survival rate of cancer patients, particularly solid tumor patients (other than blood cancer patients) who account for the majority of cancer patients is less than 50%. About two-thirds of all cancer patients are diagnosed at a progressed stage, and most of them die within 2 years after cancer diagnosis. Such poor results in cancer therapy are due not only to the problem of therapeutic methods, but also to the fact that it not easy to diagnose cancer at an early stage and to accurately diagnose progressed cancer and to carry out the follow-up of cancer patients after cancer therapy.

In current clinical practice, the diagnosis of cancer is confirmed by performing tissue biopsy after history taking, physical examination and clinical assessment, followed by radiographic testing and endoscopy if cancer is suspected. However, the diagnosis of cancer by the existing clinical practices is possible only when the number of cancer cells is more than a billion and the diameter of cancer is more than 1 cm. In this case, it is reported that the cancer cells already have metastatic ability, and at least half thereof have already metastasized. Meanwhile, tumor markers for monitoring substances that are directly or indirectly produced from cancers are used in cancer monitoring after the treatment of the cancer, but they have limitations in early diagnosis, since up to about half thereof appear normal even in the presence of cancer, and they often appear positive even in the absence of cancer.

The reason why the early diagnosis and treatment of cancer are difficult is that cancer cells significantly differ from normal cells and are highly complex and variable. Cancer cells grow excessively and continuously, invading surrounding tissue and metastasize to distal organs leading to death. Despite the attack of an immune mechanism or anticancer therapy, cancer cells survive and continually develop, and cell groups that are most suitable for survival selectively propagate. Cancer cells are living bodies with a high degree of viability, which occur by the mutation of a large number of genes. In order that one cell is converted to a cancer cell and developed to a malignant cancer lump that is detectable in clinics, the mutation of a large number of genes must occur. Thus, in order to diagnose and treat cancer at the root, approaches at a gene level are necessary.

Recently, genetic analysis has been actively attempted to diagnose cancer. The simplest typical method is to detect the presence of ABL: BCR fusion genes (the genetic characteristic of leukemia) in blood by PCR. The method has an accuracy rate of more than 95%, and after the diagnosis and therapy of chronic myelocytic leukemia using this simple and easy genetic analysis, this method is being used for the assessment of the result and follow-up study. However, this method has the deficiency that it can be applied only to some blood cancers.

Furthermore, another method has been attempted, in which the presence of genes expressed by cancer cells is detected by RT-PCR and blotting, thereby diagnosing cancer cells present in blood cells. However, this method has shortcomings in that it can be applied only to some cancers, including prostate cancer and melanoma, has a high false positive rate. In addition, it is difficult to standardize detection and reading in this method, and its utility is also limited (Kopreski, M. S. et al., *Clin. Cancer Res.*, 5:1961, 1999; Miyashiro, I. et al., *Clin. Chem.*, 47:505, 2001).

Particularly, it is known that fragmented DNAs are released from abnormal cells in the cancer tissue of cancer patients into blood flow by processes including apoptosis and necrosis, and thus exist as cell-free tumor DNA in the serum or plasma of the blood. In fact, it is known that there are frequent cases in which the concentration of DNA in the blood flow of many cancer patients is higher than that in normal people. Cancer-specifically abnormally modified DNA regions have been attempted to be used as markers for diagnosing cancer (deVos T. et al., Clin. Chem. 55:1337-1346; Potter N. T. et al., Clin. Chem. 60:9; Messaoudi S. El. et al., Clinica Chimica Acta 424:222-230; Marzese D. M. et al., Expert Rev. Mol. Diagn. 13(8):827-844).

Actually, there has been an active attempt to diagnose lung cancer, head and neck cancer, breast cancer, colon cancer, and liver cancer by examining the promoter methylation of mutated K-Ras oncogenes, p53 tumor-suppressor genes and p16 genes in serum, and the labeling and instability of microsatellite (Chen, X. Q. et al., *Clin. Cancer Res.*, 5:2297, 1999; Esteller, M. et al., *Cancer Res.*, 59:67, 1999; Sanchez-Cespedes, M. et al., *Cancer Res.*, 60:892, 2000; Sozzi, G. et al., *Clin. Cancer Res.*, 5:2689, 1999).

Meanwhile, in samples other than blood, the DNA of cancer cells can also be detected. A method has been attempted in which the presence of cancer cells or oncogenes in sputum or bronchoalveolar lavage of lung cancer patients is detected by a gene or antibody test (Palmisano, W. A. et al., *Cancer Res.*, 60:5954, 2000; Sueoka, E. et al., *Cancer Res.*, 59:1404, 1999). Additionally, another method of detecting the presence of cancer cells-derived modified genes in mucosal cells in feces of colon and rectal cancer patients (Ahlquist, D. A. et al., *Gastroenterol.*, 119:1219-27, 2000) has been attempted. However, since these gene mutations occur in some cancer patients, there is a limitation in accurately performing the early diagnosis of cancers.

In the genomic DNA of mammalian cells, there is the fifth base in addition to A, C, G and T, namely, 5-methylcytosine, in which a methyl group is attached to the fifth carbon of the cytosine ring (5-mC). 5-mC is always attached only to the C of a CG dinucleotide (5'-mCG-3'), which is frequently marked CpG. The C of CpG is mostly methylated by attachment with a methyl group. The methylation of this CpG inhibits a repetitive sequence in genomes, such as Alu or transposon, from being expressed. In addition, this CpG is a site where an epigenetic change in mammalian cells appears most often. The 5-mC of this CpG is naturally deaminated to T, and thus the CpG in mammal genomes shows only 1% of frequency, which is much lower than a normal frequency (¼×¼=6.25%).

Regions in which CpGs are exceptionally integrated are known as CpG islands. The term "CpG islands" refers to sites which are 0.2-3 kb in length, and have a C+G content of more than 50% and a CpG ratio of more than 3.75%. There are about 45,000 CpG islands in the human genome, and they are mostly found in promoter regions regulating the expression of genes. Actually, the CpG islands occur in the promoters of housekeeping genes accounting for about 50% of human genes (Cross, S. et al., Curr. Opin. Gene Develop., 5:309, 1995). It is known that aberrant DNA methylation occurs mainly in the 5' regulatory region of the gene to reduce the expression of the gene (Kane M. F. et al., Cancer Res. 57(5):808-811). Herein, the 5' regulatory region of the gene includes a promoter region, an enhancer region and a 5' untranslated region. Recently, an attempt to examine the promoter methylation of tumor-related genes in blood, sputum, saliva, feces or urine and to use the examined results for the diagnosis and treatment of various cancers, has been actively conducted (Esteller, M. et al., *Cancer Res.*, 59:67, 1999; Sanchez-Cespedez, M. et al., *Cancer Res.*, 60:892, 2000; Ahlquist, D. A. et al., *Gastroenterol.*, 119:1219, 2000). Particularly, it is well known that DNAs are released from abnormal cells in the cancer tissue of cancer patients into blood by processes including apoptosis and necrosis, and thus exist as cell-free tumor DNA in the serum or plasma of the blood, and methylated DNA fragments are also present in the cell-free tumor DNA. The presence of this aberrant DNA methylation has been used as a marker for diagnosing cancer (deVos T. et al., Clin. Chem. 55:1337-1346; Potter N. T. et al., Clin. Chem. 60:9; Messaoudi S. EI. et al., Clinica Chimica Acta 424:222-230; Marzese D. M. et al., Expert Rev. Mol. Diagn. 13(8):827-844). Accordingly, the present inventors have conducted related studies, and have found that aberrant methylation of the syndecan-2 gene can be used specifically for diagnosis of colorectal cancer and this methylation is detected in serum (KR 10-1142131 B; Oh et al., J. Mol. Diag. 15(4):498-507).

However, KR 10-1142131 B does not disclose the use of DNA methylation to detect hyperplastic cells and polyps in the clone in a pre-cancerous stage by use of a cell-free DNA sample.

It is known that aberrant DNA methylation of a specific region of a gene among epigenetic changes may occur in a pre-cancerous stage, and in some cases, aberrant methylation of a specific DNA region may also occur in the pre-cancer stage, like hyperplastic cells, cell proliferative disorders and neoplasia.

Accordingly, the present inventors have made extensive efforts to develop a methylation marker capable of detecting a cell proliferative disorder corresponding to hyperplastic cells or polyps in the clone in a precancerous stage, and as a result, have found that the 5' regulatory region of syndecan-2 gene (SDC2; NM_002998) is aberrantly methylated in colorectal tissue in a precancerous stage, and particularly, information for detection of persons having precancerous lesions can be provided by measuring frequent methylation in a cell-free DNA in the blood of these patients, thereby completing the present invention.

The information disclosed in the Background Art section is only for the enhancement of understanding of the background of the present invention, and therefore may not contain information that forms a prior art that would already be known to a person of ordinary skill in the art.

DISCLOSURE OF INVENTION

Technical Problem

It is a main object of the present invention to provide a methylation biomarker which can be effectively used for detection of precancerous lesions corresponding to a cell proliferative disorder of colon tissue, and to provide information for early detecting precancerous lesions using the methylation biomarker.

Another object of the present invention is to provide a method for detecting methylation of the SDC2 gene that is a colorectal polyp-specific methylation marker gene, the use of the SDC2 gene for detection of precancerous lesions, and a kit and nucleic acid chip for detection of precancerous lesions, which comprise the SDC2 gene.

Technical Solution

To achieve the above objects, the present invention provides a method of detecting a precancerous lesion in a subject, the method comprising the steps of:

(a) isolating a genomic DNA from a biological sample taken from the subject;

(b) measuring methylation of the CpG islands of the SDC2 (syndecan-2) gene in the isolated genomic DNA or a fragment thereof, thereby confirming the precancerous lesion.

The present invention also provides a method of detecting a precancerous lesion in a subject, the method comprising the steps of:

(a) contacting a genomic DNA isolated from a biological sample taken from the subject with at least one reagent capable of distinguishing between methylated and non-methylated CpG dinucleotides within at least one target region of the genomic DNA;

(b) determining the methylation state of the syndecan-2 gene based on the contacting; and (c) determining that the methylation of the syndecan-2 gene increases compared to that in a normal control sample, thereby detecting the precancerous lesion in the subject.

The present invention also provides a method of detecting a precancerous lesion in a subject, the method comprising the steps of:

(a) isolating a genomic DNA from a biological sample taken from the subject;

(b) treating the isolated genomic DNA or a fragment thereof with a reagent that distinguishes between methylated DNA and non-methylated DNA;

(c) contacting the treated genomic DNA or the treated fragment thereof with an amplification enzyme and at least one primer comprising, a contiguous sequence of nucleotides that is complementary to, or hybridizable under stringent conditions to at least one sequence selected from the group consisting of sequences represented by SEQ ID NOs: 1 to 5, wherein the treated genomic DNA or its fragment is either amplified to produce at least one amplification product, or is not amplified; and (d) determining the methylation state or level of one or more CpG dinucleotides selected from one or more sequences selected from the group consisting of sequences represented by SEQ ID NOs: 1 to 5, based on the presence or absence of the amplification product, thereby detecting the precancerous lesion.

The present invention also provides a modified nucleic acid for detection of a precancerous lesion, which is a nucleic acid derived from a SDC2 (syndecan-2) gene fragment represented by SEQ ID NO: 2 and which is obtained by treating the SDC2 gene fragment to convert at least one cytosine base to uracil or to another base that is detectably dissimilar to cytosine in terms of hybridization properties.

The present invention also provides a modified nucleic acid for detection of a precancerous lesion, which is a nucleic acid derived from a SDC2 (syndecan-2) gene fragment represented by SEQ ID NO: 3 and which is obtained by treating the SDC2 gene fragment to convert at least one cytosine base to uracil or to another base that is detectably dissimilar to cytosine in terms of hybridization properties.

The present invention also provides a kit for detecting a precancerous lesion, which contains a substance capable of detecting methylation of the CpG islands of an SDC2 (syndecan-2) gene.

The present invention also provides a nucleic acid chip for detecting a precancerous lesion of colorectal tissue, the nucleic acid chip having immobilized thereon a probe capable of hybridizing to a CpG island-containing fragment of the SDC2 (syndecan-2) gene under stringent conditions.

The present invention also provides a biomarker for detecting a precancerous lesion, which contains a substance capable of detecting methylation of the CpG islands of an SDC2 (syndecan-2) gene.

The present invention also provides the use of the above-described biomarker, modified nucleic acid and kit for detection of a precancerous lesion of colorectal tissue.

BRIEF DESCRIPTION OF THE DRAWINGS

FIG. 1A is a graph showing the degree of methylation of each region, and FIG. 1B shows the degrees of methylation of the promoter (left), the 5' UTR (middle) and the first intron (right) in each group.

BEST MODE FOR CARRYING OUT THE INVENTION

Figure 1A:
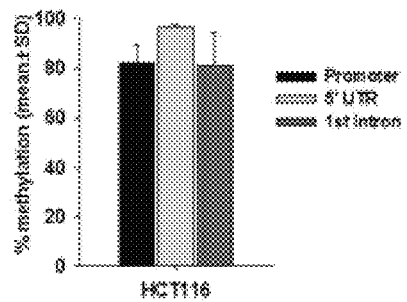
FIGS. 1A and 1B show the results of measuring the degree of methylation of the SDC2 methylation biomarker in a colorectal cancer cell line (HCT116), a normal colorectal tissue (Normal), the cancer tissue (T) of colorectal cancer patients, and a normal tissue (NT) adjacent to the cancer tissue (T), by pyrosequencing. Specifically.

Unless defined otherwise, all technical and scientific terms used herein have the same meaning as commonly understood by one of ordinary skill in the art to which the invention pertains. Generally, the nomenclature used herein and the experiment methods, which will be described below, are those well known and commonly employed in the art.

The present invention is characterized in that Methylation of the CpG islands of the syndecan-2 (SDC2) gene, which is methylated specifically in colorectal polyps or colorectal cancer, is used as a biomarker. Thus, in one aspect, the present invention is directed to a biomarker or composition for detecting precancerous lesions, which contains a substance capable of detecting CpG methylation of the syndecan-2 (SDC2) gene.

In the present invention, the CpG methylation may be located in the 5' regulatory region of the SDC2 gene, and may be present not only in the intron or 5' regulatory region of the SDC2 gene, but also in the upstream or downstream region thereof, such as an enhancer.

In the present invention, the CpG methylation may preferably be present in the promoter region, 5' untranslated region (5' UTR), exon and first intron of the SDC2 gene. Specifically, the CpG methylation may be located in a region ranging from −0.5 kb to +1.8 kb relative to the transcription start site of the SDC2 (syndecan-2) gene, that is, a region represented by SEQ ID NO: 1.

In addition, in the present invention, the CpG methylation may preferably be present in the 5' regulatory region of the SDC2 gene. Specifically, the CpG methylation may be located in a region ranging from −0.5 kb to +618 bp relative to the transcription start site of the SDC2 (syndecan-2) gene, that is, a region represented by SEQ ID NO: 2.

In an example of the present invention, it was found that the 5' untranslated region showed significantly higher sensitivity and specificity than the first intron region in diagnosis of colorectal cancer. Thus, preferably, the CpG methylation may be present in the 5' untranslated region of the SDC2 gene. Specifically, the CpG methylation may be located in a region ranging from +201 bp to +618 bp relative to the transcription start site of the SDC2 (syndecan-2) gene, that is, a region represented by SEQ ID NO: 3.

In an example of the present invention, real-time methylation-specific PCR was performed in which an isolated genomic DNA or a fragment thereof was amplified with a pair of primers having nucleotide sequences represented by SEQ ID NOs: 15 and 16 and the amplified genomic DNA or the fragment thereof was hybridized with a probe having a nucleotide sequence represented by SEQ ID NO: 17. Specifically, a genomic DNA was isolated from a biological sample taken from a subject, and methylation of the CpG islands of the SDC2 (syndecan-2) gene in the isolated genomic DNA or a fragment thereof was measured using the above-described real-time methylation-specific PCR, thereby detecting precancerous lesions (Example 3; set 1).

In another example of the present invention, real-time methylation-specific PCR was performed in which an isolated genomic DNA or a fragment thereof was amplified with a pair of primers having nucleotide sequences represented by SEQ ID NOs: 47 and 48 and the amplified genomic DNA or the treated fragment thereof was hybridized with a probe having a nucleotide sequence represented by SEQ ID NO: 49. Specifically, a genomic DNA was isolated from a biological sample taken from a subject, and methylation of the CpG islands of the SDC2 (syndecan-2) gene in the isolated genomic DNA or a fragment thereof was measured using the above-described real-time methylation-specific PCR, thereby detecting precancerous lesions (Example 4; set 2).

In still another example of the present invention, real-time methylation-specific PCR was performed in which an isolated genomic DNA or a fragment thereof was amplified with a pair of primers having nucleotide sequences represented by SEQ ID NOs: 53 and 54 and the amplified genomic DNA or the amplified fragment thereof was hybridized with a probe having a nucleotide sequence represented by SEQ ID NO: 55. Specifically, a genomic DNA was isolated from a biological sample taken from a subject, and Methylation of the CpG islands of the SDC2 (syndecan-2) gene in the isolated genomic DNA or a fragment thereof was measured using the above-described real-time methylation-specific PCR, thereby detecting precancerous lesions (Example 5; set 3)

The methylation marker gene for detecting precancerous lesions in the colon according to the present invention can also be used for polyp and cancer screening, risk assessment, prognosis, disease identification, the diagnosis of disease stages, and the selection of therapeutic targets. Particularly, it was found that the SDC2 gene that is the biomarker gene according to the present invention showed a high level and frequency of methylation positivity even in colorectal polyps, indicating that it is useful as a biomarker for diagnosis of colorectal polyps.

The identification of genes that are methylated in colorectal cancer and abnormalities at various stages of colorectal cancer makes it possible to diagnose colorectal cancer at an early stage in an accurate and effective manner and allows methylation profiling of multiple genes and the identification of new targets for therapeutic intervention. In addition, the methylation data according to the present invention may be combined with other non-methylation related biomarker detection methods to obtain a more accurate system for diagnosing precancerous lesions in the colon.

According to the method of the present invention, the progression of colorectal cancer at various stages or phases can be diagnosed by determining the methylation stage of one or more nucleic acid biomarkers obtained from a sample. By comparing the methylation stage of a nucleic acid isolated from a sample at each stage of colorectal cancer with the methylation stage of one or more nucleic acids isolated from a sample which does not have precancerous lesions corresponding to a cell proliferative disorder of colorectal tissue, a specific stage of colorectal cancer in the sample can be detected. Herein, the methylation stage may be hypermethylation.

In one embodiment of the present invention, nucleic acid may be methylated in the regulatory region of a gene. In another embodiment, a gene which is involved in cell transformation can be diagnosed at an early stage by detecting methylation outside of the regulatory region of the gene, because methylation proceeds inwards from the outside of the gene.

In an embodiment, the kit of the present invention comprises a carrier means compartmentalized to receive a sample therein, and one or more containers comprising a first container containing a reagent which sensitively cleaves unmethylated cytosine, a second container containing primers for amplification of a CpG-containing nucleic acid, and a third container containing a means to detect the presence of cleaved or uncleaved nucleic acid.

Primers that are used according to the present invention may include sequences described below, and any functional combination and fragments thereof. Herein, the functional combination or fragment is used as a primer to detect whether methylation has occurred on the genome.

In another embodiment of the present invention, a precancerous lesion of colorectal tissue in a sample can be diagnosed by detecting the methylation state of the SDC2 (syndecan-2) gene using a kit or a nucleic acid chip.

The use of the kit or nucleic acid chip for detection according to the present invention makes it possible to detect a precancerous lesion of colorectal tissue in a sample. The method comprises determining the methylation state of at least one nucleic acid isolated from a sample, wherein the methylation state of the at least one nucleic acid is compared with the methylation stage of a nucleic acid isolated from a sample in which there is no precancerous lesion of colorectal tissue.

In still another embodiment of the present invention, cells that are likely to form colorectal cancer can be diagnosed at an early stage using the methylation marker gene. When a gene confirmed to be methylated in cancer cells are methylated in cells that appear normal clinically or morphologically, this indicates that the normally appearing cells progress to cancer. Thus, transformation of the normally appearing cells into colorectal cancer diagnosed at an early stage.

The use of the methylation marker gene of the present invention allows for detection of a precancerous lesion of colorectal tissue in a sample. The detection method comprises bringing a sample comprising at least one nucleic acid isolated from a subject into contact with at least one agent capable of determining the methylation state of the nucleic acid. The method comprises detecting the methylation state of at least one region in at least one nucleic acid, wherein the methylation state of the nucleic acid differs from the methylation state of the same region of a nucleic acid present in a sample in which there is no precancerous lesion of tissue.

In yet another embodiment of the present invention, the likelihood of progression of tissue to colorectal cancer can be evaluated by examining the methylation of a gene which is methylated specifically in colorectal cancer, and determining the methylation frequency of tissue that is likely to progress to colorectal cancer.

Thus, in one aspect, the present invention is directed to a method of detecting a precancerous lesion in a subject, the method comprising the steps of:

(a) isolating a genomic DNA from a biological sample taken from the subject;

(b) measuring methylation of the CpG islands of the SDC2 (syndecan-2) gene in the isolated genomic DNA or a fragment thereof, thereby detecting the precancerous lesion.

In the present invention, the presence of methylation of the CpG islands may be indicative of the presence of a precancerous lesion. Specifically, the presence of methylation of the CpG islands or an increase in methylation of the CpG islands may be indicative of the presence of a precancerous lesion.

More specifically, step (b) in the method of the present invention may comprise measuring CpG methylation of any one of the promoter region, 5' untranslated region and intron region of the SDC2 gene. Particularly, step (b) may comprise measuring CpG methylation of a region of the SDC2 gene, which has a nucleotide sequence of SEQ ID NO: 1.

In addition, step (b) may comprise measuring methylation of CpG islands of the 5' regulatory region of the gene, wherein the CpG islands may be located in a region represented by SEQ ID NO: 2.

In addition, preferably, step (b) may comprise measuring methylation of CpG islands of the 5' untranslated region of the gene, wherein the CpG islands may be located in a region represented by SEQ ID NO: 5.

In the present invention, the measurement of methylation in step (b) may comprise treating the isolated genomic DNA or a fragment thereof with a reagent that modifies a CpG island-containing fragment to distinguish between methylated DNA and non-methylated DNA, and then measuring methylation of the treated DNA or the treated fragment thereof. Herein, the reagent that modifies a CpG island-containing fragment to distinguish between methylated DNA and non-methylated DNA may be one or more selected from among bisulfite, hydrogen sulfite, disulfite, and combinations thereof, but is not limited thereto.

A sequence modified by the reagent may be used for detection of precancerous lesions in the clone. Thus, in another aspect, the present invention is directed to a modified nucleic acid for detection of a precancerous lesion, which is a nucleic acid derived from a SDC2 (syndecan-2) gene fragment represented by SEQ ID NO: 2 and which is obtained by treating the SDC2 gene fragment to convert at least one cytosine base of the SDC2 (syndecan-2) gene fragment to uracil or to another base that is detectably dissimilar to cytosine in terms of hybridization properties. In this case, the modified nucleic acid may be represented by SEQ ID NO: 4.

Further, the present invention is directed to a modified nucleic acid for detection of a precancerous lesion, which is a nucleic acid derived from a SDC2 (syndecan-2) gene fragment represented by SEQ ID NO: 3 and which is obtained by treating the SDC2 gene fragment to convert at least one cytosine base of the SDC2 (syndecan-2) gene fragment to uracil or to another base that is detectably dissimilar to cytosine in terms of hybridization properties. In this case, the modified nucleic acid may be represented by SEQ ID NO: 5.

In the present invention, the measurement of methylation in step (b) may be performed by a method selected from the group consisting of PCR, methylation-specific PCR, real-time methylation-specific PCR, PCR using a methylated DNA specific binding protein, PCR using a methylated DNA-specific binding antibody, quantitative PCR, a nucleic acid chip method, sequencing, sequencing-by-synthesis (e.g., pyrosequencing), and sequencing-by-ligation (e.g., SOLiD system), but is not limited thereto.

In the present invention, the measurement of methylation by the sequencing or sequencing-by-synthesis method may comprise amplifying the isolated genomic DNA or a fragment thereof with one primer pair selected from the group consisting of a pair of primers represented by SEQ ID NOs: 6 and 7, a pair of primers represented by SEQ ID NOs: 9 and 10, and a pair of primers represented by SEQ ID NOs: 12 and 13, but is not limited thereto.

In the present invention, the measurement of methylation by the sequencing or sequencing-by-synthesis method may comprise amplifying the isolated genomic DNA or a fragment thereof with one sequencing primer selected from the group consisting of sequencing primers represented by SEQ ID NOs: 8, 11 and 14, but is not limited thereto.

In the present invention, the measurement of methylation by the nucleic acid chip method may comprise hybridizing the isolated genomic DNA or a fragment thereof with one probe selected from the group consisting of probes represented by SEQ ID NOs: 21 to 46, but is not limited thereto.

In the present invention, the measurement of methylation by the real-time methylation-specific PCR may comprise: amplifying the isolated genomic DNA or a fragment thereof with a pair of primers having nucleotide sequences represented by SEQ ID NOs: 15 and 16 and hybridizing the amplified genomic DNA or a fragment thereof with a probe having a nucleotide sequence represented by SEQ ID NO: 17; amplifying the isolated genomic DNA or a fragment thereof with a pair of primers having nucleotide sequences represented by SEQ ID NOs: 47 and 48 and hybridizing the amplified genomic DNA or the amplified fragment thereof with a probe having a nucleotide sequence represented by SEQ ID NO: 49; or amplifying the isolated genomic DNA or a fragment thereof with a pair of primers having nucleotide sequences represented by SEQ ID NOs: 53 and 54 and hybridizing the amplified genomic DNA or the amplified fragment thereof with a probe having a nucleotide sequence represented by SEQ ID NO: 55, but is not limited.

In another aspect, the present invention is directed to a method of detecting a precancerous lesion in a subject, the method comprising the steps of:

(a) contacting a genomic DNA isolated from a biological sample taken from the subject with at least one reagent capable of distinguishing between methylated and non-methylated CpG dinucleotides within at least one target region of the genomic DNA;

(b) determining the methylation state of the syndecan-2 gene based on the contacting; and (c) determining that the methylation of the syndecan-2 gene increases compared to that in a normal control sample, thereby detecting the precancerous lesion in the subject.

In the present invention, the reagent may be one or more selected from among bisulfite, hydrogen sulfite, disulfite, and combinations thereof, but is not limited thereto.

In still another aspect, the present invention is directed to a method of detecting a precancerous lesion in a subject, the method comprising the steps of:

(a) isolating a genomic DNA from a biological sample taken from the subject;

(b) treating the isolated genomic DNA or a fragment thereof with a reagent that distinguishes between methylated DNA and non-methylated DNA;

(c) contacting the treated genomic DNA or the treated fragment thereof with an amplification enzyme and at least one primer comprising, a contiguous sequence of nucleotides that is complementary to, or hybridizable under stringent conditions to at least one sequence selected from the group consisting of sequences represented by SEQ ID NOs: 1 to 5, wherein the treated genomic DNA or its fragment is either amplified to produce at least one amplification product, or is not amplified; and (d) determining the methylation state or level of one or more CpG dinucleotides selected from one or more sequences selected from the group consisting of sequences represented by SEQ ID NOs: 1 to 5, based on the presence or absence of the amplification product, thereby detecting the precancerous lesion.

In the present invention, the reagent may be one or more selected from among bisulfite, hydrogen sulfite, disulfite, and combinations thereof, but is not limited thereto.

In the present invention, the amplification enzyme may be a heat-resistant DNA polymerase or a polymerase having no 5' to 3' exonuclease activity, but is not limited thereto.

In the present invention, the precancerous lesion may be a colorectal polyp or colorectal cancer, but is not limited thereto.

In the present invention, the biological sample taken from the subject may be selected from cells, tissues, biopsy tissues, paraffin tissues, blood, serum, feces, urine, and combinations thereof, but is not limited thereto.

In another embodiment of the present invention, a precancerous lesion of colorectal tissue in the sample can be diagnosed by detecting the methylation state of the SDC2 syndecan-2; NM_002998) gene using a kit.

In still another embodiment of the present invention, a precancerous lesion of colorectal tissue in the sample can be diagnosed by detecting the methylation state of the SDC2 syndecan-2; NM_002998) gene using a nucleic acid chip.

Thus, in a further aspect, the present invention is directed to a kit for detecting a precancerous lesion, which contains a substance capable of detecting methylation of the CpG islands of an SDC2 (syndecan-2) gene.

In the present invention, the CpG islands may be located in the 5' regulatory region of the SDC2 gene.

In the present invention, the CpG islands may preferably be located in the promoter region, 5' untranslated region, exon or first intron of the SDC2 gene. Specifically, the CpG islands may be located in the region represented by SEQ ID NO: 1. In addition, in the present invention, the CpG islands may preferably be present in the 5' regulatory region of the SDC2 gene, and located in the region represented by SEQ ID NO: 2. Furthermore, the CpG islands may be present in the 5' untranslated region of the SDC2 gene, and located in the region represented by SEQ ID NO: 3.

In the present invention, the substance capable of detecting the methylation of the CpG islands may be at least one selected from the group consisting of a primer pair capable of amplifying a fragment containing methylated CpG islands, a probe capable of hybridizing to methylated CpG islands, a methylation-specific binding protein capable of binding to methylated CpG islands, a methylation-specific binding antibody, a methylation-sensitive restriction endonuclease, a sequencing primer, a sequencing-by-synthesis primer, and a sequencing-by-ligation primer, but is not limited thereto.

In the present invention, the fragment containing methylated CpG islands may be one nucleotide sequence selected from the group consisting of nucleotide sequences represented by SEQ ID NOs: 1 to 5, but is not limited thereto.

In the present invention, the primer pair may be any one selected from the group consisting of a pair of primers represented by SEQ ID NOs: 6 and 7, a pair of primers represented by SEQ ID NOs: 9 and 10, and a pair of primers represented by SEQ ID NOs: 12 and 13; and the sequencing primer may be any one selected from the group consisting of sequencing primers represented by SEQ ID NOs: 8, 11 and 14.

In the present invention, the probe may be any one selected from the group consisting of nucleotide sequences represented by SEQ ID NOs: 21 to 25 and 32 to 39, but is not limited thereto.

The sequences of SEQ ID NOs: 21 to 25 and 32 to 39 are as follows:

```
                                              (SEQ ID NO: 21)
5'-aaaccagaaa ctgaacctcg gcacgggaaa ggagtccgcg-3'

(SEQ ID NO: 22)
5'-gaggagcaaa accacagcag agcaagaaga gcttcagaga
gcagccttcc-3'

(SEQ ID NO: 23)
5'-actccgtgtc gggagtgcag aaaccaacaa gtgagagggc
gccgcgttcc cggggcgcag-3'

(SEQ ID NO: 24)
5'-ctgcgggcgg cgggagcagg cgcaggagga ggaagcgagc
gcccccgagc cccgagcccg-3'

(SEQ ID NO: 25)
5'-agtccccgag cctgagccgc aatcgctgcg gtactctgct
ccggattcgt gtgcgcgggc-3'

(SEQ ID NO: 32)
5'-tagaaaaggg aaagtgaaga agggaaagag aaaagacaac-3'

(SEQ ID NO: 33)
5'-ggagagagga aaagtgggga gagaaaggaa gaaaaggact
gagaaaacgc-3'

(SEQ ID NO: 34)
5'-cggagctgcc aatcggcgtg taatcctgta ggaatttctc
ccgggtttat ctgggagtca-3'

(SEQ ID NO: 35)
5'-ctgccgtagc tcccttttcaa gccagcgaat ttattcctta-3'

(SEQ ID NO: 36)
5'-gcacgggaaa ggagtccgcg gaggagcaaa accacagcag
agcaagaaga-3'

(SEQ ID NO: 37)
5'-gcagccttcc cggagcacca actccgtgtc gggagtgcag
aaaccaacaa gtgagagggc-3'

(SEQ ID NO: 38)
5'-gccgcgttcc cggggcgcag ctgcgggcgg cgggagcagg
cgcaggagga ggaagcgagc-3'

(SEQ ID NO: 39)
5'-gcccccgagc cccgagcccg agtccccgag cctgagccgc
aatcgctgcg gtactctgct-3'
```

In the present invention, the probe may be hybridized to a converted nucleic acid fragment obtained by treating a CpG island-containing fragment with a reagent that distinguishes between methylated DNA and non-methylated DNA; and the probe may be any one selected from the group consisting of nucleotide sequences represented by SEQ ID NOs: 26 to 31 and 40 to 46, but is not limited thereto.

The sequences of SEQ ID NOs: 26 to 31 and 40 to 46 are as follows:

```
                                              (SEQ ID NO: 26)
5'-TGTCGTAGTTTTTTTTTAAGTTAGCGAA-3'

(SEQ ID NO: 27)
5'-AATTTCGGTACGGGAAAGGAGTTCGCGGAGGA-3'

(SEQ ID NO: 28)
5'-GTTTTTTCGGAGTATTAATTTCGTGTCGGGAGTGTAGAAATTA
A-3'

(SEQ ID NO: 29)
5'-GTGAGAGGGCGTCGCGTTTTCGGGGCGTAGTTGCGGGCGGCGGG
AG-3'

(SEQ ID NO: 30)
5'-GGCGTAGGAGGAGGAAGCGAGCGTTTTCGAGTTTCGAGTTC
GAGTTT-3'

(SEQ ID NO: 31)
5'-TCGAGTTTGAGTCGTAATCGTTGCGGTATTTTGTTTCGGATTC
GTGTGCGCGGGTTG-3'

(SEQ ID NO: 40)
5'-AGAAAACGTAGGAGTTTTGGTTTGTCGG-3'
```

-continued (SEQ ID NO: 41)
5'-TAGAGTCGGCGTAGTTATAGCGCGGAGTCGCG-3'

(SEQ ID NO: 42)
5'-TTCGGGTTTATTTGGGAGTTATATTGTCGTTTTTTT-3'

(SEQ ID NO: 43)
5'-GAGTTCGGAGAAGTAGGTTTAGGAGGGAGGGAGTTAG
AGGAAAAGAAGAGGAGGAGA-3'

(SEQ ID NO: 44)
5'-CGGGGAGGGAGGCGCGGCGCGGGAGGAGGAGGGGCGTAGT
CGCGG-3'

(SEQ ID NO: 45)
5'-CGGATCGCGCGTTTTCGTCGTTTTGTTTT-3'

(SEQ ID NO: 46)
5'-GAATTTCGGTACGGGAAAGGAGTTCGCGG-3'

In the present invention, the primer pair may have nucleotide sequences represented by SEQ ID NOs: 15 and 16, and the probe may have a nucleotide sequence represented by SEQ ID NO: 17. Alternatively, the primer pair may have nucleotide sequences represented by SEQ ID NOs: 47 and 48, and the probe may have a nucleotide sequence represented by SEQ ID NO: 49. Alternatively, the primer pair may have nucleotide sequences represented by SEQ ID NOs: 53 and 54, and the probe may have a nucleotide sequence represented by SEQ ID NO: 55. However, the scope of the present invention is not limited thereto.

In the present invention, the precancerous lesion may be a colorectal hyperplastic polyp or adenomatous polyp.

In a still further aspect, the present invention is directed to a nucleic acid chip for detecting a precancerous lesion of colorectal tissue, the nucleic acid chip having immobilized thereon a probe capable of hybridizing to a CpG island-containing fragment of an SDC2 (syndecan-2) gene under stringent conditions.

In the present invention, the fragment containing methylated CpG islands may be a nucleotide sequence selected from the group consisting of nucleotide sequences represented by SEQ ID NOs: 1 to 5, but is not limited thereto.

In the present invention, the probe may be any one selected from the group consisting of nucleotide sequences represented by SEQ ID NOs: 21 to 25 and 32 to 39.

In addition, in the present invention, the probe may be a probe capable of hybridizing to a converted fragment obtained by treating a CpG island-containing fragment with a reagent such as bisulfite, that is, a reagent that distinguishes between methylated DNA and non-methylated DNA. In an embodiment, the probe may be any one selected from the group consisting of nucleotide sequences represented by SEQ ID NOs: 26 to 31 and 39 to 46.

The probes represented by SEQ ID NOs: 32 to 39 are probes capable of hybridizing to a CpG island-containing fragment of the promoter or 5' regulatory region of the SDC2 (syndecan-2) gene.

The use of the kit or nucleic acid chip for detection according to the present invention allows for detection of a precancerous lesion of colorectal tissue in a sample. The method comprises determining the methylation state of at least one nucleic acid isolated from a sample, wherein the methylation state of the at least one nucleic acid is compared with the methylation stage of a nucleic acid isolated from a sample in which there is no precancerous lesion of colorectal tissue.

In another embodiment of the present invention, transformed colorectal cells can be detected by examining methylation of the marker gene using the above-described kit or nucleic acid chip.

In still another embodiment of the present invention, colorectal cancer can be diagnosed by examining methylation of the marker gene using the above-described kit or nucleic acid chip.

In yet another embodiment of the present invention, the likelihood of progression of tissue to colorectal cancer can be evaluated by examining methylation of the marker gene using the above-described kit or nucleic acid chip in comparison with a sample showing a normal phenotype. The sample may be any one selected from among solid or liquid tissue, cells, feces, urine, blood, serum and plasma.

In a yet further aspect, the present invention is directed to a biomarker or composition for detecting a precancerous lesion, which contains a substance capable of detecting methylation of the CpG islands of an SDC2 (syndecan-2) gene.

In the present invention, the CpG methylation may be present in the 5' regulatory region of the SDC2 gene.

In the present invention, the CpG islands may be located in a region having one nucleotide sequence selected from the group consisting of nucleotide sequences represented by SEQ ID NOs: 1 to 5, but are not limited thereto.

In the present invention, the substance capable of detecting methylation of the CpG islands may be one or more selected from the group consisting of a primer pair capable of amplifying a fragment containing methylated CpG islands, a probe capable of hybridizing to methylated CpG islands, a methylation-specific binding protein capable of binding to methylated CpG islands, a methylation-specific binding antibody, a methylation-sensitive restriction endonuclease, a sequencing primer, a sequencing-by-synthesis primer, and a sequencing-by-ligation primer, but is not limited thereto.

In the present invention, the fragment containing methylated CpG islands may be any one nucleotide sequence selected from the group consisting of nucleotide sequences represented by SEQ ID NOs: 1 to 5, but is not limited thereto.

In the present invention, the primer pair may be any one selected from the group consisting of a pair of primers represented by SEQ ID NOs: 6 and 7, a pair of primers represented by SEQ ID NOs: 9 and 10, and a pair of primers represented by SEQ ID NOs: 12 and 13; and the sequencing primer may be any one selected from the group consisting of sequencing primers represented by SEQ ID NOs: 8, 11 and 14.

In the present invention, the probe may be any one selected from the group consisting of nucleotide sequences represented by SEQ ID NOs: 21 to 25 and 32 to 39, but is not limited thereto.

In the present invention, the probe may be hybridized to a converted nucleic acid fragment obtained by treating a CpG island-containing fragment with a reagent that distinguishes between methylated DNA and non-methylated DNA; and the probe may be any one selected from the group consisting of nucleotide sequences represented by SEQ ID NOs: 26 to 31 and 40 to 46, but is not limited thereto.

In the present invention, the primer pair may have nucleotide sequences represented by SEQ ID NOs: 15 and 16, and the probe may have a nucleotide sequence represented by SEQ ID NO: 17. Alternatively, the primer pair may have nucleotide sequences represented by SEQ ID NOs: 47 and 48, and the probe may have a nucleotide sequence represented by SEQ ID NO: 49. Alternatively, the primer pair may have nucleotide sequences represented by SEQ ID NOs: 53 and 54, and the probe may have a nucleotide sequence represented by SEQ ID NO: 55. However, the scope of the present invention is not limited thereto.

In the present invention, the precancerous lesion may be a colorectal hyperplastic polyp or adenomatous polyp.

In another aspect, the present invention is directed to the use of the above-described biomarker, modified nucleic acid and kit for detection of a precancerous lesion of colorectal tissue.

The definition of main terms used herein is as follows.

As used herein, the term "cell transformation" refers to the change in characteristics of a cell from one form to another form such as from normal to abnormal, non-tumorous to tumorous, undifferentiated to differentiated, stem cell to non-stem cell. In addition, the transformation can be recognized by the morphology, phenotype, biochemical characteristics and the like of a cell.

As used herein, the term "early detection" of cancer refers to discovering the likelihood of cancer prior to metastasis, and preferably before observation of a morphological change in a tissue or cell. Furthermore, the term "early detection" of cell transformation refers to the high probability of a cell to undergo transformation in its early stages before the cell is morphologically designated as being transformed.

As used herein, the term "hypermethylation" refers to the methylation of a CpG island.

As used herein, the term "sample" or "clinical sample" is referred to in its broadest sense, and includes any biological sample obtained from an individual, body fluid, a cell line, a tissue culture, depending on the type of assay that is to be performed. Methods for obtaining tissue biopsies and body fluids from mammals are well known in the art. A tissue biopsy of the colon is a preferred source.

Biomarker for Colon Cancer—Use of Cancer Cells for Comparison with Normal Cells

In the present invention, "normal" cells refer to those that do not show any abnormal morphological or cytological changes. "Tumor" cells are cancer cells. "Non-tumor" cells are those cells that are part of the diseased tissue but are not considered to be the tumor portion.

In another embodiment of the present invention, a cellular proliferative disorder of colon tissue cell can be diagnosed at an early stage by determining the methylation stage of at least one nucleic acid from a subject using the kit or nucleic acid chip of the present invention. Herein, the methylation stage of the at least one nucleic acid may be compared with the methylation state of at least one nucleic acid isolated from a subject not having a cellular proliferative disorder of colon tissue. The nucleic acid is preferably a CpG-containing nucleic acid such as a CpG island.

In another embodiment of the present invention, a cellular proliferative disorder of colon tissue can be diagnosed by determining the methylation of at least one nucleic acid from a subject using the kit or nucleic acid chip of the present invention. Herein, the nucleic acid may be SDC2 (NM_002998, Syndecan 2). In this embodiment, the methylation of the at least one nucleic acid may be compared with the methylation state of at least one nucleic acid isolated from a subject having no predisposition to a cellular proliferative disorder of colon tissue.

As used herein, the term "predisposition" refers to the property of being susceptible to a cellular proliferative disorder. A subject having a predisposition to a cellular proliferative disorder has no cellular proliferative disorder, but is a subject having an increased likelihood of having a cellular proliferative disorder.

In another aspect, the present invention provides a method for diagnosing a cellular proliferative disorder of colon tissue, the method comprising brining a sample comprising a nucleic acid into contact with an agent capable of determining the methylation state of the sample, and determining the methylation of at least one region of the at least one nucleic acid. Herein, the methylation of the at least one region in the at least one nucleic acid differs from the methylation stage of the same region in a nucleic acid present in a subject in which there is no abnormal growth of cells.

The method of the present invention comprises a step of determining the methylation of at least one region of at least one nucleic acid isolated from a subject. The term "nucleic acid" or "nucleic acid sequence" as used herein refers to an oligonucleotide, nucleotide or polynucleotide, or fragments thereof, or single-stranded or double-stranded DNA or RNA of genomic or synthetic origin, sense- or antisense-strand DNA or RNA of genomic or synthetic origin, peptide nucleic acid (PNA), or any DNA-like or RNA-like material of natural or synthetic origin. It will apparent to those of skill in the art that, when the nucleic acid is RNA, the deoxynucleotides A, G, C, and T are replaced by the ribonucleotides A, G, C, and U, respectively.

Any nucleic acid may be used in the present invention, as long as the presence of differently methylated CpG islands can be detected therein. The CpG island is a CpG-rich region in a nucleic acid sequence.

Methylation

In the present invention, any nucleic acid sample, in purified or nonpurified form, can be used, provided it contains or is suspected of containing a nucleic acid sequence containing a target locus (e.g., CpG-containing nucleic acid). One nucleic acid region capable of being differentially methylated is a CpG island, a sequence of nucleic acid with an increased density relative to other nucleic acid regions of the dinucleotide CpG. The CpG doublet occurs in vertebrate DNA at only about 20% of the frequency that would be expected from the proportion of G*C base pairs. In certain regions, the density of CpG doublets reaches the predicted value; it is increased by ten-fold relative to the rest of the genome. CpG islands have an average G*C content of about 60%, compared with the 40% average in bulk DNA. The CpG islands take the form of stretches of DNA typically about one to two kilobases long. There are about 45,000 CpG islands in the human genome.

In various genes, CpG islands are present mainly in the 5' regulatory region of the genes. The 5' regulatory region includes the promoter, 5' untranslated region and enhancer region of the gene.

Typically, the CpG-containing nucleic acid is DNA. However, the inventive method may employ, for example, samples that contain DNA, or DNA and RNA containing mRNA, wherein DNA or RNA may be single-stranded or double-stranded, or a DNA-RNA hybrid may be included in the sample.

A mixture of nucleic acids may also be used. The specific nucleic acid sequence to be detected may be a fraction of a larger molecule or can be present initially as a discrete molecule, so that the specific sequence constitutes the entire nucleic acid. It is not necessary that the sequence to be studied be present initially in a pure form; the nucleic acid may be a minor fraction of a complex mixture, such as contained in whole human DNA. Nucleic acids contained in a sample used for detection of methylated CpG islands may be extracted by a variety of techniques such as that described by Sambrook, et al. (Molecular Cloning: A Laboratory Manual, Cold Spring Harbor, N.Y., 1989).

Nucleic acids isolated from a subject are obtained in a biological sample from the subject. If it is desired to detect colon cancer or stages of colon cancer progression, the nucleic acid may be isolated from colon tissue, feces, blood, serum, plasma or urine. Such samples may be obtained by various medical procedures known to those of skill in the art.

In one aspect of the invention, the state of methylation in nucleic acids of the sample obtained from a subject is hypermethylation compared with the same regions of the nucleic acid in a subject not having a cellular proliferative disorder of colon tissue. Hypermethylation as used herein refers to the presence of methylated alleles in one or more nucleic acids. Nucleic acids from a subject not having a cellular proliferative disorder of colon tissue contain no detectable methylated alleles when the same nucleic acids are examined.

Individual Genes and Panel

It is understood that the present invention may be practiced using each gene separately as a diagnostic or prognostic marker, or several marker genes combined into a panel display format so that several marker genes may be methylated to increase reliability and efficiency. Furthermore, any of the genes identified in the present invention may be used individually or as a set of genes in any combination with any of the other genes that are recited herein. Alternatively, genes may be ranked according to their importance and weighted and together with the number of genes that are methylated, a level of likelihood of developing cancer may be assigned. Such algorithms are within the scope of the present invention.

Method for Detection of Methylation

Methylation-Specific PCR

When genomic DNA is treated with bisulfite, cytosine in the 5'-CpG'-3 region remains intact, if it was methylated, but the cytosine changes to uracil, if it was unmethylated. Accordingly, based on the base sequence converted after bisulfite treatment, PCR primer sets corresponding to a region having the 5'-CpG-3' base sequence are constructed. Herein, the constructed primer sets are two kinds of primer sets: a primer set corresponding to the methylated base sequence, and a primer set corresponding to the unmethylated base sequence. When genomic DNA is converted with bisulfite and then amplified by PCR using the above two kinds of primer sets, the PCR product is detected in the PCR mixture employing the primers corresponding to the methylated base sequence, if the genomic DNA was methylated, but the genomic DNA is detected in the PCR mixture employing the primers corresponding to the unmethylated, if the genomic DNA was unmethylated. This methylation can be quantitatively analyzed by agarose gel electrophoresis.

Real-Time Methylation Specific PCR

Real-time methylation-specific PCR is a real-time measurement method modified from the methylation-specific PCR method and comprises treating genomic DNA with bisulfite, designing PCR primers corresponding to the methylated base sequence, and performing real-time PCR using the primers. Methods of detecting the methylation of the genomic DNA include two methods: a method of detection using a TanMan probe complementary to the amplified base sequence; and a method of detection using Sybergreen. Thus, the real-time methylation-specific PCR allows selective quantitative analysis of methylated DNA. Herein, a standard curve is plotted using an in vitro methylated DNA sample, and a gene containing no 5'-CpG-3' sequence in the base sequence is also amplified as a negative control group for standardization to quantitatively analyze the degree of methylation.

Pyrosequencing

The pyrosequencing method is a quantitative real-time sequencing method modified from the bisulfite sequencing method. Similarly to bisulfite sequencing, genomic DNA is converted by bisulfite treatment, and then, PCR primers corresponding to a region containing no 5'-CpG-3' base sequence are constructed. Specifically, the genomic DNA is treated with bisulfite, amplified using the PCR primers, and then subjected to real-time base sequence analysis using a sequencing primer. The degree of methylation is expressed as a methylation index by quantitatively analyzing the amounts of cytosine and thymine in the 5'-CpG-3' region.

PCR Using Methylated DNA-Specific Binding Protein, Quantitative PCR, and DNA Chip Assay When a protein binding specifically only to methylated DNA is mixed with DNA, the protein binds specifically only to the methylated DNA. Thus, either PCR using a methylation-specific binding protein or a DNA chip assay allows selective isolation of only methylated DNA. Genomic DNA is mixed with a methylation-specific binding protein, and then only methylated DNA was selectively isolated. The isolated DNA is amplified using PCR primers corresponding to the promoter region, and then methylation of the DNA is measured by agarose gel electrophoresis.

In addition, methylation of DNA can also be measured by a quantitative PCR method, and methylated DNA isolated with a methylated DNA-specific binding protein can be labeled with a fluorescent probe and hybridized to a DNA chip containing complementary probes, thereby measuring methylation of the DNA. Herein, the methylated DNA-specific binding protein may be, but not limited to, MBD2bt.

Detection of Differential Methylation-Methylation-Sensitive Restriction Endonuclease Detection of differential methylation can be accomplished by bringing a nucleic acid sample into contact with a methylation-sensitive restriction endonuclease that cleaves only unmethylated CpG sites.

In a separate reaction, the sample is further brought into contact with an isoschizomer of the methylation-sensitive restriction enzyme that cleaves both methylated and unmethylated CpG-sites, thereby cleaving the methylated nucleic acid.

Specific primers are added to the nucleic acid sample, and the nucleic acid is amplified by any conventional method. The presence of an amplified product in the sample treated with the methylation-sensitive restriction enzyme but absence of an amplified product in the sample treated with the isoschizomer of the methylation-sensitive restriction enzyme indicates that methylation has occurred at the nucleic acid region assayed. However, the absence of an amplified product in the sample treated with the methylation-sensitive restriction enzyme together with the absence of an amplified product in the sample treated with the isoschizomer of the methylation-sensitive restriction enzyme indicates that no methylation has occurred at the nucleic acid region assayed.

As used herein, the term "methylation-sensitive restriction enzyme" refers to a restriction enzyme (e.g., SmaI) that includes CG as part of its recognition site and has activity when the C is methylated as compared to when the C is not methylated. Non-limiting examples of methylation-sensitive restriction enzymes include MspI, HpaII, BssHII, BstUI and NotI. Such enzymes can be used alone or in combination.

Examples of other methylation-sensitive restriction enzymes include, but are not limited to SacII and EagI.

The isoschizomer of the methylation-sensitive restriction enzyme is a restriction enzyme that recognizes the same recognition site as the methylation-sensitive restriction enzyme but cleaves both methylated and unmethylated CGs. An example thereof includes MspI.

Primers of the present invention are designed to be "substantially" complementary to each strand of the locus to be amplified and include the appropriate G or C nucleotides as discussed above. This means that the primers must be sufficiently complementary to hybridize with their respective strands under polymerization reaction conditions. Primers of the present invention are used in the amplification process, which is an enzymatic chain reaction (e.g., PCR) in which that a target locus exponentially increases through a number of reaction steps. Typically, one primer is homologous with the negative (−) strand of the locus (antisense primer), and the other primer is homologous with the positive (+) strand (sense primer). After the primers have been annealed to denatured nucleic acid, the nucleic acid chain is extended by an enzyme such as DNA Polymerase I (Klenow), and reactants such as nucleotides, and, as a result, + and − strands containing the target locus sequence are newly synthesized. When the newly synthesized target locus is used as a template and subjected to repeated cycles of denaturing, primer annealing, and extension, exponential synthesis of the target locus sequence occurs. The resulting reaction product is a discrete nucleic acid duplex with termini corresponding to the ends of specific primers employed.

The amplification reaction is PCR which is commonly used in the art. However, alternative methods such as real-time PCR or linear amplification using isothermal enzyme may also be used. In addition, multiplex amplification reactions may also be used.

Detection of Differential Methylation—Bisulfate Sequencing Method

Another method for detecting a methylated CpG-containing nucleic acid comprises the steps of: bringing a nucleic acid-containing sample into contact with an agent that modifies unmethylated cytosine; and amplifying the CpG-containing nucleic acid in the sample using CpG-specific oligonucleotide primers, wherein the oligonucleotide primers distinguish between modified methylated nucleic acid and non-methylated nucleic acid and detect the methylated nucleic acid. The amplification step is optional and desirable, but not essential. The method relies on the PCR reaction to distinguish between modified (e.g., chemically modified) methylated DNA and unmethylated DNA. Such methods are described in U.S. Pat. No. 5,786,146 relating to bisulfite sequencing for detection of methylated nucleic acid.

Bisulfite Sequencing Method

Another method for detecting a methylated CpG-containing nucleic acid comprises the steps of: contacting a nucleic acid-containing sample with an agent that modifies a non-methylated cytosine; and amplifying the CpG-containing nucleic acid in the sample by means of methylation-independent oligonucleotide primers. Herein, the oligonucleotide primers can amplify the nucleic acid without distinguishing modified methylated and non-methylated nucleic acids. The amplified product may be sequenced by the Sanger method using a sequencing primer or by a next-generation sequencing method linked with bisulfite sequencing for detection of methylated nucleic acid.

Herein, the next-generation sequencing method may be performed by sequencing-by-synthesis and sequencing-by-ligation. This method is characterized in that a single DNA fragment is spatially separated in place of making a bacterial clone, and is amplified in situ (clonal amplification) and sequenced. Herein, it analyzes hundreds of thousands of fragments at the same time, and thus is called "massively parallel sequencing".

It is based on sequencing-by-synthesis, and relies on a method of obtaining a signal while sequentially attaching mono- or di-nucleotides. It includes pyrosequencing, ion torrent and Solexa methods.

NGS systems based on sequencing-by synthesis include a Roche 454 platform, an Illumina HiSeq platform, an Ion PGM platform (Life Technology), and a PacBio platform (Pacific BioSciences). The 454 and Ion PGM platforms use emersion PCR that is a clonal amplification method, and the HiSeq platform uses Bridge amplification. The sequencing-by-synthesis method analyzes a sequence by detecting phosphate which is generated when synthesizing a DNA while sequentially attaching single nucleotides, hydrogen ion, or a pre-labeled fluorescence dye. To detect a sequence, the 454 platform uses a pyrosequencing method employing phosphate, and the Ion PGM platform uses hydrogen ion detection. The HiSeq and PacBio platforms analyze a sequence by detecting fluorescence.

Sequencing-by-ligation is a sequencing technique employing DNA ligase, and is performed by identifying nucleotides at specific positions in a DNA nucleotide sequence. Unlike most sequencing techniques employing polymerase, sequencing-by-ligation does not use a polymerase, and uses the characteristic in that DNA ligase does not ligate a mismatch sequence. It includes a SOLiD system. In this technique, two bases are read in each step, and the reading steps are independently repeated five times through the primer reset process. Thus, each base is read twice to increase accuracy.

In the case of sequencing-by-ligation, among dinucleotide primer sets made of 16 combinations, dinucleotide primers corresponding to the nucleotide sequence of interest are sequentially ligated, and a combination of the ligations is analyzed, thereby determining the nucleotide sequence of the DNA of interest.

Sequencing, Sequencing-by-Synthesis or Sequencing-by-Ligation Using Methylated DNA-Specific Binding Protein or Antibody In a sequencing or next-generation sequencing method using a methylated DNA-specific binding protein or antibody, only a methylated DNA can be isolated, because when a protein or antibody that binds specifically to a methylated DNA is mixed with the DNA, the protein or antibody binds specifically to the methylated DNA. In the present invention, a genomic DNA was mixed with a methylated DNA-specific binding protein, and then only a methylated DNA was selectively separated therefrom. The separated DNA was amplified using PCR primers, and then methylation of the amplified DNA was measured by the Sanger method, the sequencing-by-synthesis method or the sequencing-by-ligation method.

Herein, the next-generation sequencing method may be performed by sequencing-by-synthesis or sequencing-by-ligation. Herein, the methylated DNA-specific binding protein is not limited to MBD2bt, and the antibody is not limited to a 5'-methyl-cytosine antibody.

Kit

The present invention provides a kit useful for the detection of a cellular proliferative disorder in a subject. The kit of the present invention may comprise a substance capable of detecting Methylation of the CpG islands of a gene.

As one example, the kit of the present invention comprises a carrier means compartmentalized to receive a sample therein, one or more containers comprising a second container containing PCR primers for amplification of a 5'-CpG-3' base sequence, and a third container containing a probe for detecting an amplified PCR product.

Carrier means are suited for containing one or more containers such as vials, tubes, and the like, each of the containers comprising one of the separate elements to be used in the method. In view of the description provided herein of the inventive method, those of skill in the art can readily determine the apportionment of the necessary reagents among the containers.

Substrates

After the target nucleic acid region has been amplified, the nucleic acid amplification product can be hybridized to a known gene probe attached to a solid support (substrate) to detect the presence of the nucleic acid sequence.

As used herein, the term "substrate", when used in reference to a substance, structure, surface or material, means a composition comprising a nonbiological, synthetic, nonliving, planar or round surface that is not heretofore known to comprise a specific binding, hybridization or catalytic recognition site or a plurality of different recognition sites or a number of different recognition sites which exceeds the number of different molecular species comprising the surface, structure or material. Examples of the substrate include, but are not limited to, semiconductors, synthetic (organic) metals, synthetic semiconductors, insulators and dopants; metals, alloys, elements, compounds and minerals; synthetic, cleaved, etched, lithographed, printed, machined and microfabricated slides, devices, structures and surfaces; industrial polymers, plastics, membranes silicon, silicates, glass, metals and ceramics; and wood, paper, cardboard, cotton, wool, cloth, woven and nonwoven fibers, materials and fabrics; and amphibious surfaces.

It is known in the art that several types of membranes have adhesion to nucleic acid sequences. Specific non-limiting examples of these membranes include nitrocellulose or other membranes used for detection of gene expression such as polyvinylchloride, diazotized paper and other commercially available membranes such as GENE-SCREEN™, ZETAPROBE™ (Biorad) and NYTRAN™. Beads, glass, wafer and metal substrates are also included. Methods for attaching nucleic acids to these objects are well known in the art. Alternatively, screening can be done in a liquid phase.

Hybridization Conditions

In nucleic acid hybridization reactions, the conditions used to achieve a particular level of stringency will vary depending on the nature of the nucleic acids being hybridized. For example, the length, degree of complementarity, nucleotide sequence composition (e.g., GC/AT content), and nucleic acid type (e.g., RNA/DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at room temperature (hybridization conditions); 0.2×SSC/0.1% SDS at room temperature (low stringency conditions); 0.2×SSC/0.1% SDS at 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary depending on the particular hybridization reaction involved, and can be determined empirically. In general, conditions of high stringency are used for the hybridization of the probe of interest.

Label

The probe of interest can be detectably labeled, for example, with a radioisotope, a fluorescent compound, a bioluminescent compound, a chemiluminescent compound, a metal chelator, or an enzyme. Appropriate labeling with such probes is widely known in the art and can be performed by any conventional method.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1: Selection of Optimum Methylation Region of SDC2 Gene for Detection of Colorectal Precancerous Lesion In order to select the optimum methylation region for detection of a colorectal precancerous lesion and to confirm the methylation state of the SDC2 methylation biomarker gene, pyrosequencing of the CpG islands of the SDC2 genes was performed.

In order to modify non-methylated cytosine to uracil using bisulfite, total genomic DNA was isolated from each of the colorectal cancer cell line HCT116 (Korea Cell Line Bank (KCLB) No. 10247), normal colorectal tissue (Biochain), and colorectal cancer tissue and a normal tissue adjacent thereto (the Biobank, the Yonsei University Medical Center), and 200 ng of the genomic DNA was treated with bisulfite using the EZ DNA methylation-gold kit (Zymo Research, USA). When the DNA was treated with bisulfite, non-methylated cytosine was modified to uracil, and the methylated cytosine remained without changes. The DNA treated with bisulfite was eluted in 20 μl of sterile distilled water and subjected to pyrosequencing.

In order to perform pyrosequencing of the SDC2 gene, PCR and sequencing primers for the promoter, 5' untranslated region and first intron region of the gene PCR and sequencing primers for performing pyrosequencing for the 7 genes were designed using PSQ assay design program (Biotage, USA). The PCR and sequencing primers for measuring the methylation of each of the regions are shown in Table 1.

TABLE 1

Primers for bisulfite-PCR and pyrosequencing

| Regions | Primers | Sequences (5'->3')[a] | SEQ ID NOS | Size of amplicon (bp) |
|---|---|---|---|---|
| Promoter | Forward | AAAGATAAAGGGGAAGAAAAGAGTATAGAGG | 6 | 204 |
|  | Reverse | Biotin-CCCAAATAAACCCCAAAAAAATTCCTACAAAA | 7 |  |
|  | Sequencing | AAGGAAGAAAAGGATTGA | 8 |  |
| 5' untranslated region | Forward | GGGAGTAGGAGTAGGAGGAGGAA | 9 | 149 |
|  | Reverse | Biotin-ACCAAAACAAAACCAAACCTCCTACCCA | 10 |  |
|  | Sequencing | AGTAGGAGTAGGAGGAGGAA | 11 |  |
| 1st intron | Forward | YGTTTTTYGAGATTAGGGATGATT | 12 | 107 |
|  | Reverse | Biotin-TCTCCCCAAAACTTACAT | 13 |  |
|  | Sequencing | GGGATGATTTGGAAATT | 14 |  |

20 ng of the genomic DNA treated with bisulfite was amplified by PCR. In the PCR amplification, a PCR reaction solution (20 ng of the genomic DNA treated with bisulfite, 5 μl of 10×PCR buffer (Enzynomics, Korea), 5 units of Taq polymerase (Enzynomics, Korea), 4 μl of 2.5 mM dNTP, and 2 μl (10 pmole/μl) of PCR primers) was used, and the PCR reaction was performed under the following conditions: predenaturation at 95° C. for 5 min, and then 45 cycles of denaturation at 95° C. for 40 sec, annealing at 60° C. for 45 sec and extension at 72° C. for 40 sec, followed by final extension at 72° C. for 5 min. The amplification of the PCR product was confirmed by electrophoresis on 2.0% agarose gel.

[a]Y=C or T.

The amplified PCR product was treated with PyroGold reagents (Biotage, USA), and then subjected to pyrosequencing using the PSQ96MA system (Biotage, USA) in accordance with the manufacturer's instruction. After the pyrosequencing, the methylation degree of the DNA was measured by calculating the methylation index. The methylation index was calculated by determining the average rate of cytosine binding to each CpG island.

Figure 1B:
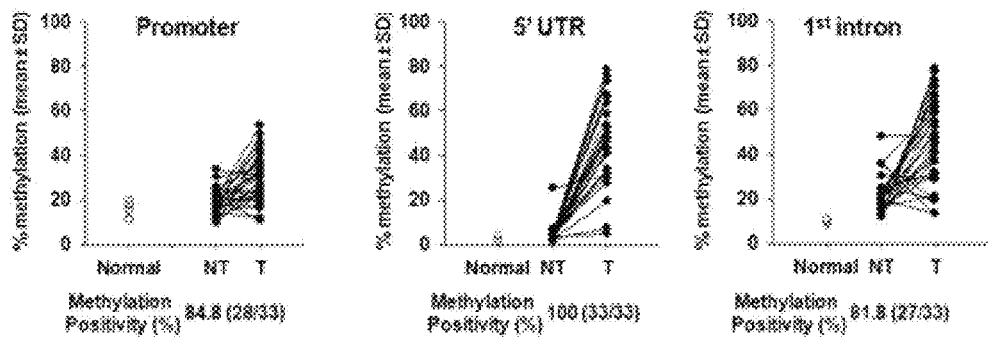

The methylation of each region of the SDC2 gene in the colorectal cancer cell line was measured. As a result, it was shown that the 5' untranslated region of the gene was methylated at a level higher than the promoter and intron regions, and the promoter and intron regions were methylated at similar levels (FIG. 1A). The methylation of each region of the SDC2 gene in normal colorectal tissue (Normal) was measured, and as a result, it was shown that the methylation level of the 5' regulatory region was very lower than those of the promoter and intron regions. Such results indicate that the 5' regulatory region has higher specificity than the promoter and intron regions in the diagnosis of colorectal cancer. In addition, the methylation of each region of the SDC2 gene in the cancer tissue (T) and normal colorectal tissue (NT) adjacent thereto of 33 colorectal cancer patients was measured, and as a result, it was observed that the frequency of methylation positivity was highest in the 5' regulatory region (100%; 33/33) ($P<0.0001$), and was the second highest in the promoter region (84.8%; 28/33), and was the lowest in the intron region (81.8%; 27/33). Such results indicate that the 5' regulatory region of the SDC2 gene has the best diagnostic performance in the diagnosis of colorectal cancer (FIG. 1B).

Figure 2A:
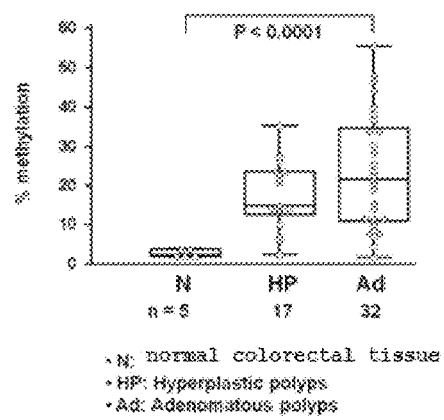
FIG. 2A shows the results of measuring the methylation of the SDC2 methylation biomarker in normal colorectal tissue (N) and colorectal polyp tissues (HP and Ad)

Example 2: Verification of Methylation of SDC2 Methylation Marker Gene in Colorectal Precancerous Lesions In order to evaluate the ability of the SDC2 methylation marker gene to detect a colorectal polyp that is a precancerous lesion, pyrosequencing of the 5' regulatory region confirmed to have the best diagnostic performance in Example 1 was performed. As a result, it was shown that the 5' regulatory region was not substantially methylated (less than 5%) in normal colorectal tissue (N), but was methylated at very high levels in a hyperplastic polyp (HP) and an adenomatous polyp (Ad) ($P<0.0001$, Kruskal-Wallis test, MedC 및 program, Belgium) (FIG. 2A)

Figure 2B:
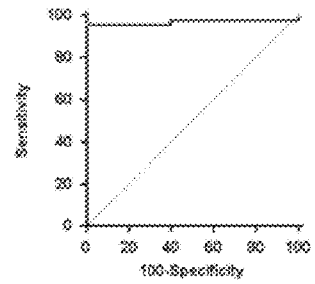
FIG. 2B shows the results of ROC curve analysis performed to evaluate the diagnostic ability of the biomarker.

In order to evaluate the ability of the SDC2 methylation marker gene to detect colorectal polyps, the sensitivity and specificity of the SDC2 gene for colorectal polyp diagnosis were measured by ROC curve analysis (MedCalc Program, Belgium) (FIG. 2B). As shown in FIG. 2B, it was shown that the sensitivity of the SDC2 methylation marker gene for polyp diagnosis was 95.9% (47/49), and the specificity was 100%, indicating that the SDC2 methylation marker gene is highly useful for polyp diagnosis. The above results suggest that the SDC2 methylation marker gene is highly useful for colorectal polyp diagnosis.

Example 3: Verification of SDC2 Methylation Gene in Sera of Colorectal Precancerous Lesion Patients by Use of Set 1 Primer Pair and Probe In order to verify whether the SDC2 methylation biomarker gene is useful for detection of the precancerous lesion colorectal polyp in serum DNA sample, genomic DNA was isolated from the each of the sera of 36 colonoscopy-confirmed normal control sera (BioServe, USA), 10 hyperplastic polyp patient sera (BioServe, USA), 28 colorectal adenomatous polyp patient sera (the Biobank, the Yonsei University Medical Center) and 39 colorectal cancer patient sera (the Biobank, the Yonsei University Medical Center). Genomic DNA was isolated from 1.0 mL of each of the sera using the ChargeSwitch gDNA 1 mL Serum Kit (Invitrogen, USA).

The isolated genomic DNA was treated with bisulfite using the EZ DNA methylation-Gold kit (Zymo Research, USA), and then eluted with 10 μl of sterile distilled water and subjected to methylation-specific real-time PCR (qMSP; Methylation-Specific real time PCR).

For quantitative methylation-specific PCR (qMSP) of the genomic DNA treated with bisulfite, real-time PCR (Rotor Gene-Q, Qiagen, Germany) of the genomic DNA was performed using the EpiTect MethyLight Master Mix (w/o) ROX (Qiagen, Cat. No. 59496, Germany) according to the manufacturer's instruction. To amplify the COL2A1 gene as an internal control, a 1/5 volume of the bisulfite-treated DNA was used as a template, and to amplify the 5' regulatory region of the SDC2 methylation biomarker gene, a 4/5 volume of the bisulfite-treated DNA was used as a template. qMSP was performed using a final volume of 20 μl with a mixture (10 μl of 2× EpiTect MethyLight Master Mix (w/o) ROX, 1 μl of PCR primer (each 4.0 pmole/μl) and 1 μl of TaqMan probe (4 pmole/μl). The qMSP was performed under the following conditions: predenaturation at 95° C. for 5 min, and then 40 cycles, each consisting of 95° C. for 15 sec and 61° C. for 60. The amplification of the PCR product was confirmed by measuring the Ct (cycling threshold) value. The sequences of primers for qMSP and probes for detection are shown in Table 2 below.

TABLE 2

Sequences of amplification primers for qMSP and probes for detection

| Genes | Primers and probes | Sequences | SEQ ID NOS | Size of amplified product (bp) |
|---|---|---|---|---|
| SDC2 | F | TAGAAATTAATAAGTGAGAGGGCGT | 15 | 121 |
| | R | GACTCAAACTCGAAAACTCG AA | 16 | |
| | Probe | FAM-AGTAGGCGTAGGAGGAGG AAGCGA | 17 | |
| COL2A1 | F | GTAATGTTAGGAGTATTTTGTGGGTA | 18 | 86 |
| | R | CTACCCCAAAAAAACCCAATCCTA | 19 | |
| | Probe FAM- | 20 AGAAGAAGGGAGGGGTGTTAGGAGAGG | | |

Figure 3A:
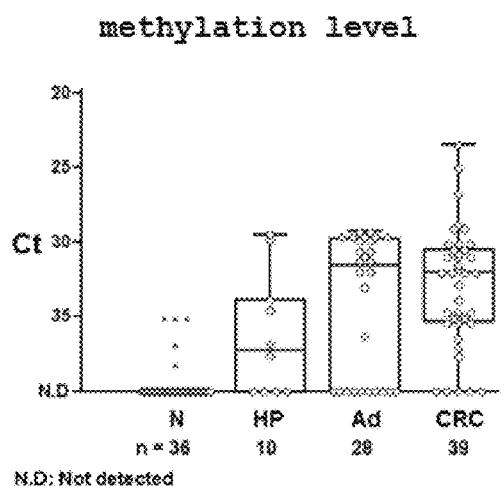
FIG. 3A shows the results of measuring methylation in the sera of normal persons (N) conformed to be normal by colonoscopy, colorectal polyp patients (Polyp) and colorectal cancer patients, by quantitative methylation-specific PCR (qMSP) using Set 1 primers and a probe.

As a result, as shown in FIG. 3A, no methylation was detected in 31 of the 36 normal persons confirmed by colonoscopy, and a low level of methylation was detected only in 5 of the 36 normal persons. However, in the colorectal polyp patients (n=38; size: 1 cm or less), methylation was detected at a very high level and frequency (P<0.0001, Kruskal Wallis test).

Figure 3B:
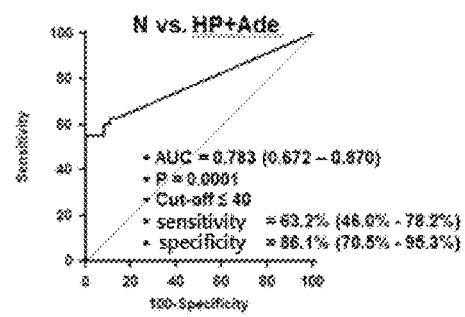
FIG. 3B shows the results of ROC curve analysis performed to evaluate the ability to detect colorectal polyps.
Figure 3B:
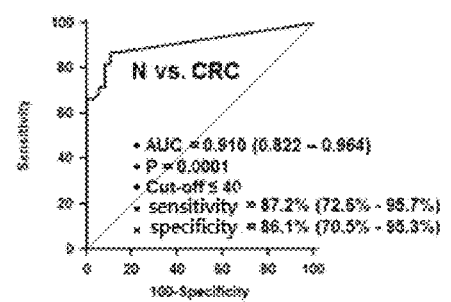

In order to evaluate the ability of the SDC2 methylation biomarker gene to diagnose colorectal polyps in serum DNA samples, the sensitivity and sensitivity of the SDC2 gene for colorectal polyp diagnosis were measured by ROC curve analysis (MedCalc Program, Belgium) (FIG. 3B). As a result, it was shown that the sensitivity of the SDC2 gene for colorectal polyp diagnosis was 63.2% (24/38), and the specificity of the SDC2 gene for colorectal polyp diagnosis was 86.1%. In addition, the sensitivity of the SDC2 gene for colorectal hyperplastic polyps was 60.0% (6/10), and the sensitivity of the SDC2 gene for colorectal adenomatous polyps was as high as 64.3% (18/28). This indicates that the SDC2 methylation biomarker gene is useful for diagnosis of colorectal polyps in sera. In addition, in order to evaluate the ability of the SDC2 methylation biomarker gene to diagnose colorectal cancer in serum DNA samples, the sensitivity and specificity of the SDC2 gene for colorectal cancer diagnosis were measured by ROC curve analysis (MedCalc Program, Belgium). As a result, it was found that the sensitivity of the SDC2 gene for colorectal cancer diagnosis was 87.2% (34/39), and the specificity of the SDC2 gene for colorectal cancer diagnosis was 86.1%. Such results suggest that the SDC2 methylation biomarker gene is highly useful for early diagnosis of colorectal cancer in serum.

Example 4: Verification of SDC2 Methylation Gene in Sera of Colorectal Precancerous Lesion Patients by Use of Set 2 Primer Pair and Probe In order to verify whether the SDC2 methylation biomarker gene is useful for detection of the precancerous lesion colorectal polyp in serum DNA sample, genomic DNA was isolated from the each of the sera of 52 colonoscopy-confirmed normal control sera (BioServe, USA), 10 hyperplastic polyp patient sera (BioServe, USA), 51 colorectal adenomatous polyp patient sera (the Biobank, the Yonsei University Medical Center) and 29 colorectal cancer patient sera (the Biobank, the Yonsei University Medical Center). Genomic DNA was isolated from 1.0 mL of each of the sera using the ChargeSwitch gDNA 1 mL Serum Kit (Invitrogen, USA).

The isolated genomic DNA was treated with bisulfite using the EZ DNA methylation-Gold kit (Zymo Research, USA), and then eluted with 10 μl of sterile distilled water and subjected to methylation-specific real-time PCR (qMSP; Methylation-Specific real time PCR).

For quantitative methylation-specific PCR (qMSP) of the genomic DNA treated with bisulfite, real-time PCR (Rotor Gene-Q, Qiagen, Germany) of the genomic DNA was performed using the EpiTect MethyLight Master Mix (w/o) ROX (Qiagen, Cat. No. 59496, Germany) according to the manufacturer's instruction. To amplify the COL2A1 gene as an internal control, a 1/5 volume of the bisulfite-treated DNA was used as a template, and to amplify the 5' regulatory region of the SDC2 methylation biomarker gene, a 4/5 volume of the bisulfite-treated DNA was used as a template. qMSP was performed using a final volume of 20 μl with a mixture (4 μl of 5× Apta Taq DNA Master (Roche Diagnostics), 2 μl of PCR primer (each 5.0 pmole/μl) and 2 μl of TaqMan probe (4 pmole/μl). The qMSP was performed under the following conditions: predenaturation at 95° C. for 5 min, and then 40 cycles, each consisting of 95° C. for 15 sec and 61° C. for 60. The amplification of the PCR product was confirmed by measuring the Ct (cycling threshold) value. The sequences of primers for qMSP and probes for detection re shown in Table 2 below.

TABLE 3

Sequences of amplification primers for qMSP and probes for detection

| Genes | Primers and probes | Sequences | SEQ ID NOS | Size of amplified product (bp) |
|---|---|---|---|---|
| SDC2 | F | GTAGAAATTAATAAGTGAGAGGGC | 47 | 124 |
|  | R | ACGACTCAAACTCGAAAACTCG | 48 |  |
|  | Probe | FAM-TTCGGGGCGTAGTTGCGGGCGG | 49 |  |
| COL2A1 | F | GTAATGTTAGGAGTATTTTGTGGGTA | 50 | 86 |
|  | R | CTACCCCAAAAAAACCCAATCCTA | 51 |  |
|  | Probe | FAM-AGAAGAAGGGAGGGGTGTTAGGAGAGG | 52 |  |

Figure 4A:
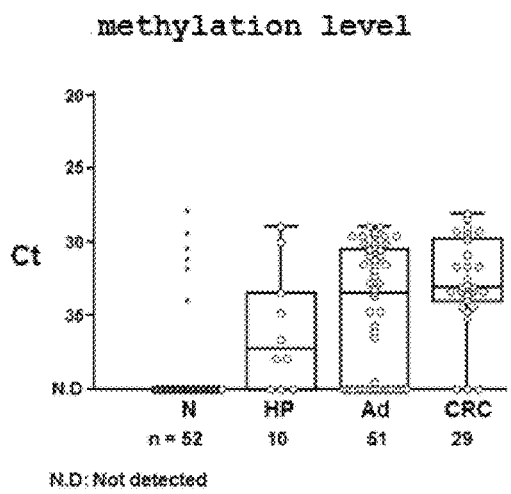
FIG. 4A shows the results of measuring methylation in the sera of colonoscopy-confirmed normal persons (N), colorectal polyp patients (Polyp) and colorectal cancer patients by qMSP using Set 2 primers and a probe.

As a result, as shown in FIG. 4A, no methylation was detected in 46 of the 52 normal persons confirmed by colonoscopy, and a low level of methylation was detected only in 6 of the 52 normal persons. However, in the colorectal polyp patients (n=61; size: 1 cm or less), methylation was detected at a very high level and frequency (P<0.0001, Kruskal Wallis test).

Figure 4B:
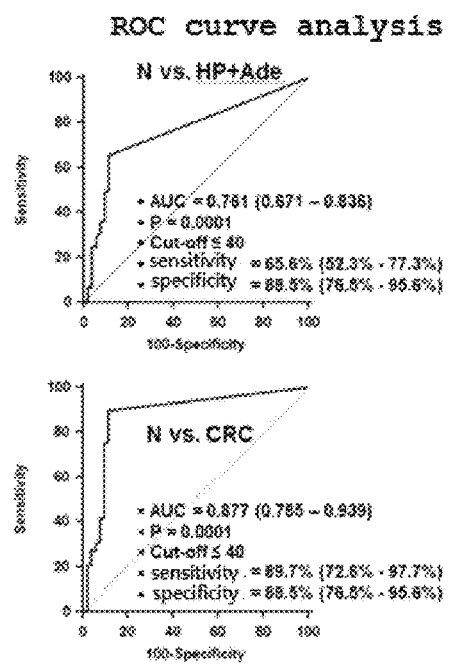
FIG. 4B shows the results of ROC curve analysis performed to evaluate the ability to detect colorectal polyps.

In order to evaluate the ability of the SDC2 methylation biomarker gene to diagnose colorectal polyps in serum DNA samples, the sensitivity and sensitivity of the SDC2 gene for colorectal polyp diagnosis were measured by ROC curve analysis (MedCalc Program, Belgium) (FIG. 4B). As a result, it was shown that the sensitivity of the SDC2 gene for colorectal polyp diagnosis was 65.6% (40/61), and the specificity of the SDC2 gene for colorectal polyp diagnosis was 88.5%. In addition, the sensitivity of the SDC2 gene for colorectal hyperplastic polyps was 70.0% (7/10), and the sensitivity of the SDC2 gene for colorectal adenomatous polyps was as high as 64.7% (33/51). This indicates that the SDC2 methylation biomarker gene is useful for diagnosis of colorectal polyps in sera. In addition, in order to evaluate the ability of the SDC2 methylation biomarker gene to diagnose colorectal cancer in serum DNA samples, the sensitivity and specificity of the SDC2 gene for colorectal cancer diagnosis were measured by ROC curve analysis (MedCalc Program, Belgium). As a result, it was found that the sensitivity of the SDC2 gene for colorectal cancer diagnosis was 89.7% (26/29), and the specificity of the SDC2 gene for colorectal cancer diagnosis was 89.7%. Such results suggest that the SDC2 methylation biomarker gene is highly useful for early diagnosis of colorectal cancer in serum.

Example 5: Verification of SDC2 Methylation Gene in Sera of Colorectal Precancerous Lesion Patients by Use of Set 3 Primer Pair and Probe In order to verify whether the SDC2 methylation biomarker gene is useful for detection of the precancerous lesion colorectal polyp in serum DNA sample, genomic DNA was isolated from the each of the sera of 51 colonoscopy-confirmed normal control sera (BioServe, USA), 10 hyperplastic polyp patient sera (BioServe, USA), 72 colorectal adenomatous polyp patient sera (the Biobank, the Yonsei University Medical Center) and 117 colorectal cancer patient sera (the Biobank, the Yonsei University Medical Center). Genomic DNA was isolated from 1.0 mL of each of the sera using the ChargeSwitch gDNA 1 mL Serum Kit (Invitrogen, USA).

The isolated genomic DNA was treated with bisulfite using the EZ DNA methylation-Gold kit (Zymo Research, USA), and then eluted with 10 µl of sterile distilled water and subjected to methylation-specific real-time PCR (qMSP; Methylation-Specific real time PCR).

For quantitative methylation-specific PCR (qMSP) of the genomic DNA treated with bisulfite, real-time PCR (Rotor Gene-Q, Qiagen, Germany) of the genomic DNA was performed using the EpiTect MethyLight Master Mix (w/o) ROX (Qiagen, Cat. No. 59496, Germany) according to the manufacturer's instruction. To amplify the COL2A1 gene as an internal control, a 1/5 volume of the bisulfite-treated DNA was used as a template, and to amplify the 5' regulatory region of the SDC2 methylation biomarker gene, a 4/5 volume of the bisulfite-treated DNA was used as a template. qMSP was performed using a final volume of 20 µl with a mixture (4 µl of 5x Apta Taq DNA Master (Roche Diagnostics), 2 µl of PCR primer (each 5.0 pmole/µl) and 2 µl of TaqMan probe (4 pmole/µl). The qMSP was performed under the following conditions: predenaturation at 95° C. for 5 min, and then 40 cycles, each consisting of 95° C. for 15 sec and 61° C. for 60. The amplification of the PCR product was confirmed by measuring the Ct (cycling threshold) value. The sequences of primers for qMSP and probes for detection re shown in Table 2 below.

TABLE 4

Sequences of amplification primers for qMSP and probes for detection

| Genes | Primers and probes | Sequences | SEQ ID NOS | Size of amplified product (bp) |
|---|---|---|---|---|
| SDC2 | F | GTAGAAATTAATAAGTGAGAIGGC | 53 | 124 |
|  | R | ACGACTCAAACTCGAAAAITCG | 54 |  |
|  | Probe | FAM-TTCGGGGCGTAGTTGCGGGCGG | 55 |  |

TABLE 4-continued

Sequences of amplification primers for qMSP and probes for detection

| Genes | Primers and probes | Sequences | SEQ ID NOS | Size of amplified product (bp) |
|---|---|---|---|---|
| COL2A1 | F | GTAATGTTAGGAGTATTTTGTGGITA | 56 | 86 |
|  | R | CTAICCAAAAAAACCCAATCCTA | 57 |  |
|  | Probe | FAM-AGAAGAAGGGAGGGGTGTTA GGAGAGG | 58 |  |

Figure 5A:
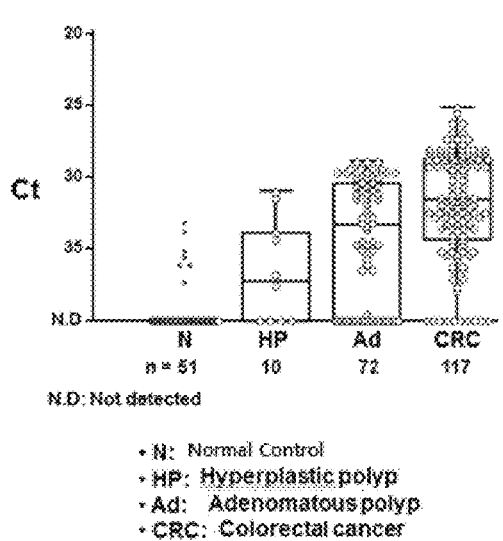
FIG. 5A shows the results of measuring methylation in the sera of colonoscopy-confirmed normal persons (N), colorectal polyp patients (Polyp) and colorectal cancer patients by qMSP using Set 3 primers and a probe.

As a result, as shown in FIG. 5A, no methylation was detected in 44 of the 51 normal persons confirmed by colonoscopy, and a low level of methylation was detected only in 7 of the 51 normal persons. However, in the colorectal polyp patients (n=82; size: 1 cm or less), methylation was detected at a very high level and frequency (P<0.0001, Kruskal Wallis test).

Figure 5B:
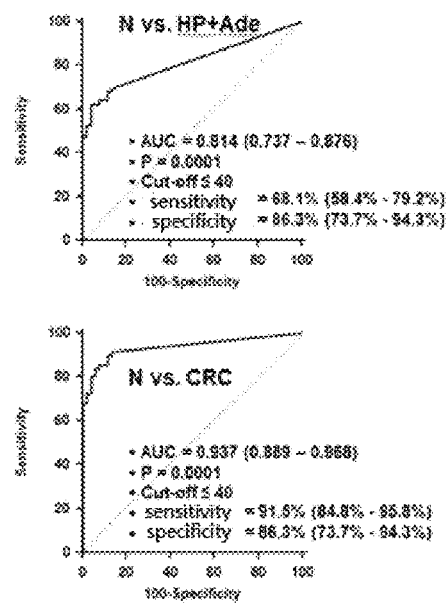
FIG. 5B shows the results of ROC curve analysis performed to evaluate the ability to detect colorectal polyps.

In order to evaluate the ability of the SDC2 methylation biomarker gene to diagnose colorectal polyps in serum DNA samples, the sensitivity and sensitivity of the SDC2 gene for colorectal polyp diagnosis were measured by ROC curve analysis (MedCalc Program, Belgium) (FIG. 5B). As a result, it was shown that the sensitivity of the SDC2 gene for colorectal polyp diagnosis was 69.5% (57/82), and the specificity of the SDC2 gene for colorectal polyp diagnosis was 86.3%. In addition, the sensitivity of the SDC2 gene for colorectal hyperplastic polyps was 60.0% (6/10), and the sensitivity of the SDC2 gene for colorectal adenomatous polyps was as high as 68.1% (49/72). This indicates that the SDC2 methylation biomarker gene is useful for diagnosis of colorectal polyps in sera. In addition, in order to evaluate the ability of the SDC2 methylation biomarker gene to diagnose colorectal cancer in serum DNA samples, the sensitivity and specificity of the SDC2 gene for colorectal cancer diagnosis were measured by ROC curve analysis (MedCalc Program, Belgium). As a result, it was found that the sensitivity of the SDC2 gene for colorectal cancer diagnosis was 89.7% (26/29), and the specificity of the SDC2 gene for colorectal cancer diagnosis was 89.7%. Such results suggest that the SDC2 methylation biomarker gene is highly useful for early diagnosis of colorectal cancer in serum.

INDUSTRIAL APPLICABILITY

As described above, the present invention provides the method of providing information for diagnosis of precancerous lesions, particularly colorectal hyperplastic polyps or adenomatous polyps, by detecting methylation of the CpG islands of the gene for detecting precancerous lesions.

The use of the method, composition, kit and nucleic acid chip for methylation detection according to the present invention makes it possible to diagnose colorectal precancerous lesions at an early transformation stage, thus enabling the early diagnosis of colorectal precancerous lesions. In addition, the methylation detection method of the present invention enables colorectal precancerous lesions to be effectively diagnosed in an accurate and rapid manner compared to conventional methods.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method of detecting a CpG methylation of SDC2 (syndecan-2) gene, the method comprising the steps of:
   (a) isolating a genomic DNA from a biological sample selected from the group consisting of colorectal tissue samples and serum samples taken from a subject;
   (b) measuring methylation of a CpG of the 5' UTR of SDC2 (syndecan-2) gene in the isolated genomic DNA or a fragment thereof by methylation-specific real time PCR (qMSP) with a primer pair, SEQ ID NOs: 47 and 48, or SEQ ID NOs: 53 and 54.

2. The method of claim 1, wherein the measurement of methylation in step (b) comprises treating the isolated genomic DNA or a fragment thereof with a reagent that modifies a CpG island-containing fragment to distinguish between methylated DNA and non-methylated DNA, and then measuring methylation of the treated DNA or the treated fragment thereof.

3. The method of claim 2, wherein the reagent is one or more selected from among bisulfate, hydrogen sulfite, disulfite, and combinations thereof.

4. The method of claim 1, further comprising detecting an amplified product produced by the primer pair using a probe of SEQ ID NO: 49 or 55.

* * * * *

UNITED STATES PATENT AND TRADEMARK OFFICE
CERTIFICATE OF CORRECTION

PATENT NO. : 10,266,900 B2
APPLICATION NO. : 14/900149
DATED : April 23, 2019
INVENTOR(S) : Sungwhan An Page 1 of 1

It is certified that error appears in the above-identified patent and that said Letters Patent is hereby corrected as shown below:

In the Specification

In Columns 23-24, Line 19, insert the following footnote of Table 1: -- [a] Y = C or T --.

Signed and Sealed this
Fourth Day of June, 2019

Andrei Iancu
*Director of the United States Patent and Trademark Office*

SEQUENCE LISTING

```
<160> NUMBER OF SEQ ID NOS: 58

<210> SEQ ID NO 1
<211> LENGTH: 2340
<212> TYPE: DNA
<213> ORGANISM: Homo sapiens

<400> SEQUENCE: 1
ttgggggtgc ggaaggattt gggagaatgg gaaacactct cactatatat ttattacatt      60
aattatcttc tcttttaaaa tgcaattttc atgaactggc gatttatgaa cacttcacat     120
tgcttgaaag catcttacac ttttttttttc cctcaactca caaagcagtt tctttctact     180
ggtcgaattc tcaaggcaga aaagctacat acgtctctcg tttcttcact aattgttctc     240
tagaaaaggg aaagtgaaga agggaaagag aaaagacaac ggggaagaaa agagcataga     300
ggagagagga aaagtgggga gagaaggaa gaaaaggact gagaaaacgc aggagccctg     360
gcttgccggt gagcagagcc ggcgcagcca cagcgcggag ccgcggcgcc cactggtcct     420
cggagctgcc aatcggcgtg taatcctgta ggaatttctc ccgggtttat ctgggagtca     480
```

```
cactgccgcc tcctctcccc agtcgcccag gggagcccgg agaagcaggc tcaggaggga      540
gggagccaga ggaaaagaag aggaggagaa ggaggaggac ccggggaggg aggcgcggcg      600
cgggaggagg aggggcgcag ccgcggagcc agtggcccg cttggacgcg ctgctctcca       660
gatacccccg gagctccagc cgcgcggatc gcgcgctccc gccgctctgc ccctaaactt      720
ctgccgtagc tccctttcaa gccagcgaat ttattcctta aaaccagaaa ctgaacctcg      780
gcacgggaaa ggagtccgcg gaggagcaaa accacagcag agcaagaaga gcttcagaga      840
gcagccttcc cggagcacca actccgtgtc gggagtgcag aaaccaacaa gtgagagggc      900
gccgcgttcc cggggcgcag ctgcgggcgg cgggagcagg cgcaggagga ggaagcgagc      960
gcccccgagc cccgagcccg agtccccgag cctgagccgc aatcgctgcg gtactctgct     1020
ccggattcgt gtgcgcgggc tgcgccgagc gctgggcagg aggcttcgtt ttgccctggt     1080
tgcaagcagc ggctgggagc agccggtccc tggggaatat gcggcgcgcg tggatcctgc     1140
tcaccttggg cttggtggcc tgcgtgtcgg cggagtcgag agcagagctg acatctgata     1200
aagacatgta ccttgacaac agctccattg aagaagcttc aggagtgtat cctattgatg     1260
acgatgacta cgcttctgcg tctggctcgg gagctgatga ggatgtagag agtccagagc     1320
tgacaacatc tcgaccactt ccaaagatac tgttgactag tgctgctcca aaagtggaaa     1380
ccacgacgct gaatatacag aacaagatac ctgctcagac aaagtcacct gaagaaactg     1440
ataaagagaa agttcacctc tctgactcag aaaggaaaat ggacccagcc gaagaggata     1500
caaatgtgta tactgagaaa cactcagaca gtctgtttaa acggacagaa gtcctagcag     1560
ctgtcattgc tggtggagtt attggctttc tctttgcaat ttttcttatc ctgctgttgg     1620
tgtatcgcat gagaaagaag gatgaaggaa gctatgacct ggagaacgc aaaccatcca      1680 gtgctgctta tcagaaggca cctactaagg agttttatgc gtaaaactcc aacttagtgt     1740
ctctatttat gagatcactg aacttttcaa aataaagctt ttgcatagaa taatgaagat     1800
ctttgttttt tgttttcatt aaagagccat tctggcactt taatgataaa atcccattgt     1860
atttaaaaca tttcatgtat ttctttagaa caacataaaa ttaaaattta acatctgcag     1920
tgttctgtga atagcagtgg caaaatatta tgttatgaaa accctcgatg ttcatggaat     1980
tggtttaaac ttttatgcgc aaatacaaaa tgattgtctt tttcctatga ctcaaagatg     2040
aaagctgttt catttgtgtc agcatgtctc agattgacct taccaagttg gtcttacttt     2100
gttaatttat ctgttgtccc cttcctctcc tctgccctcc cttcttgtgc ccttaaaacc     2160
aaaccctatg cctttgtag ctgtcatggt gcaatttgtc tttggaaaat tcagataatg      2220
gtaatttagt gtatatgtga ttttcaaata tgtaaacttt aacttccact ttgtataaat     2280
ttttaagtgt cagactatcc tcaccttggg cttggtggcc tgcgtgtcgg cggagtcggt     2340
```

<210> SEQ ID NO 2
<211> LENGTH: 1180
<212> TYPE: DNA
<213> ORGANISM: Homo sapiens

<400> SEQUENCE: 2

```
ttggggggtgc ggaaggattt gggagaatgg gaaacactct cactatatat ttattacatt      60
aattatcttc tcttttaaaa tgcaattttc atgaactggc gatttatgaa cacttcacat     120
tgcttgaaag catcttacac ttttttttttc cctcaactca caaagcagtt tctttctact     180
ggtcgaattc tcaaggcaga aaagctacat acgtctctcg tttcttcact aattgttctc     240
tagaaaaggg aaagtgaaga agggaaagag aaaagacaac ggggaagaaa agagcataga     300
```

```
ggagagagga aaagtgggga gagaaaggaa gaaaaggact gagaaaacgc aggagccctg        360
gcttgccggt gagcagagcc ggcgcagcca cagcgcggag ccgcggcgcc cactggtcct        420
cggagctgcc aatcggcgtg taatcctgta ggaatttctc ccgggtttat ctgggagtca        480
cactgccgcc tcctctcccc agtcgcccag gggagcccgg agaagcaggc tcaggaggga        540
gggagccaga ggaaaagaag aggaggagaa ggaggaggac ccggggaggg aggcgcggcg        600
cgggaggagg aggggcgcag ccgcggagcc agtggccccg cttggacgcg ctgctctcca        660
gatacccccg gagctccagc cgcgcggatc gcgcgctccc gccgctctgc ccctaaactt        720
ctgccgtagc tcccttttcaa gccagcgaat ttattcctta aaaccagaaa ctgaacctcg        780
gcacgggaaa ggagtccgcg gaggagcaaa accacagcag agcaagaaga gcttcagaga        840
gcagccttcc cggagcacca actccgtgtc gggagtgcag aaaccaacaa gtgagagggc        900
gccgcgttcc cggggcgcag ctgcgggcgg cgggagcagg cgcaggagga ggaagcgagc        960
gcccccgagc ccgagcccg agtccccgag cctgagccgc aatcgctgcg gtactctgct       1020
ccggattcgt gtgcgcgggc tgcgccgagc gctgggcagg aggcttcgtt ttgccctggt       1080
tgcaagcagc ggctgggagc agccggtccc tggggaatat gcggcgcgcg tggatcctgc       1140
tcaccttggg cttggtggcc tgcgtgtcgg cggagtcggt                             1180

<210> SEQ ID NO 3
<211> LENGTH: 618
<212> TYPE: DNA
<213> ORGANISM: Homo sapiens

<400> SEQUENCE: 3
agtcgcccag gggagcccgg agaagcaggc tcaggaggga gggagccaga ggaaaagaag         60
aggaggagaa ggaggaggac ccggggaggg aggcgcggcg cgggaggagg aggggcgcag        120
ccgcggagcc agtggccccg cttggacgcg ctgctctcca gatacccccg gagctccagc        180
cgcgcggatc gcgcgctccc gccgctctgc ccctaaactt ctgccgtagc tcccttttcaa       240 gccagcgaat ttattcctta aaaccagaaa ctgaacctcg gcacgggaaa ggagtccgcg        300
gaggagcaaa accacagcag agcaagaaga gcttcagaga gcagccttcc cggagcacca        360
actccgtgtc gggagtgcag aaaccaacaa gtgagagggc gccgcgttcc cggggcgcag        420
ctgcgggcgg cgggagcagg cgcaggagga ggaagcgagc gcccccgagc ccgagcccg        480 agtccccgag cctgagccgc aatcgctgcg gtactctgct ccggattcgt gtgcgcgggc        540
tgcgccgagc gctgggcagg aggcttcgtt ttgccctggt tgcaagcagc ggctgggagc        600
agccggtccc tggggaat                                                      618

<210> SEQ ID NO 4
<211> LENGTH: 1180
<212> TYPE: DNA
<213> ORGANISM: Artificial Sequence
<220> FEATURE:
<223> OTHER INFORMATION: Bisulfite treated SDC2 gene fragment

<400> SEQUENCE: 4
ttgggggtgc ggaaggattt gggagaatgg gaaatatttt tattatatat ttattatatt         60
aattattttt tttttaaaa tgtaattttt atgaattggc gatttatgaa tattttatat        120
tgtttgaaag tattttatat ttttttttt ttttaattta taaagtagtt ttttttatt         180 ggtcgaattt ttaaggtaga aaagttatat acgttttcg tttttttatt aattgttttt        240
```

```
tagaaaaggg aaagtgaaga agggaaagag aaaagataac ggggaagaaa agagtataga      300
ggagagagga aaagtgggga gagaaaggaa gaaaaggatt gagaaaacgt aggagttttg      360
gtttgtcggt gagtagagtc ggcgtagtta tagcgcggag tcgcggcgtt tattggtttt      420
cggagttgtt aatcggcgtg taattttgta ggaatttttt tcgggtttat ttgggagtta      480
tattgtcgtt ttttttttt agtcgtttag gggagttcgg agaagtaggt ttaggaggga      540
gggagttaga ggaaaagaag aggaggagaa ggaggaggat tcggggaggg aggcgcggcg      600
cgggaggagg aggggcgtag tcgcggagtt agtggtttcg tttggacgcg ttgtttttta      660
gatattttcg gagttttagt cgcgcggatc gcgcgttttc gtcgttttgt ttttaaattt      720
ttgtcgtagt ttttttttaa gttagcgaat ttattttta aaattagaaa ttgaatttcg      780
gtacgggaaa ggagttcgcg gaggagtaaa attatagtag agtaagaaga gttttagaga      840
gtagtttttt cggagtatta atttcgtgtc gggagtgtag aaattaataa gtgagagggc      900
gtcgcgtttt cggggcgtag ttgcgggcgg cggagtagg cgtaggagga ggaagcgagc      960
gttttcgagt ttcgagttcg agttttcgag tttgagtcgt aatcgttgcg gtattttgtt     1020
tcggattcgt gtgcgcgggt tgcgtcgagc gttgggtagg aggtttcgtt ttgttttggt     1080
tgtaagtagc ggttgggagt agtcggtttt tggggaatat gcggcgcgcg tggattttgt     1140
ttattttggg tttggtggtt tgcgtgtcgg cggagtcggt                           1180
```

<210> SEQ ID NO 5
<211> LENGTH: 618
<212> TYPE: DNA
<213> ORGANISM: Artificial Sequence
<220> FEATURE:
<223> OTHER INFORMATION: Bisulfite treated 5'UTR of SDC2

<400> SEQUENCE: 5

```
agtcgtttag gggagttcgg agaagtaggt ttaggaggga gggagttaga ggaaaagaag       60
aggaggagaa ggaggaggat tcggggaggg aggcgcggcg cgggaggagg aggggcgtag      120
tcgcggagtt agtggtttcg tttggacgcg ttgtttttta gatattttcg gagttttagt      180
cgcgcggatc gcgcgttttc gtcgttttgt ttttaaattt ttgtcgtagt ttttttttaa      240
gttagcgaat ttattttta aaattagaaa ttgaatttcg gtacgggaaa ggagttcgcg      300
gaggagtaaa attatagtag agtaagaaga gttttagaga gtagtttttt cggagtatta      360
atttcgtgtc gggagtgtag aaattaataa gtgagagggc gtcgcgtttt cggggcgtag      420
ttgcgggcgg cggagtagg cgtaggagga ggaagcgagc gttttcgagt ttcgagttcg      480
agttttcgag tttgagtcgt aatcgttgcg gtattttgtt tcggattcgt gtgcgcgggt      540
tgcgtcgagc gttgggtagg aggtttcgtt ttgttttggt tgtaagtagc ggttgggagt      600
agtcggtttt tggggaat                                                   618
```

<210> SEQ ID NO 6
<211> LENGTH: 31
<212> TYPE: DNA
<213> ORGANISM: Artificial Sequence
<220> FEATURE:
<223> OTHER INFORMATION: primer for promoter

<400> SEQUENCE: 6

```
aaagataaag gggaagaaaa gagtatagag g                                     31
```

<210> SEQ ID NO 7
<211> LENGTH: 32

<212> TYPE: DNA
<213> ORGANISM: Artificial Sequence
<220> FEATURE:
<223> OTHER INFORMATION: primer for promoter

<400> SEQUENCE: 7
cccaaataaa ccccaaaaaa attcctacaa aa                                    32

<210> SEQ ID NO 8
<211> LENGTH: 18
<212> TYPE: DNA
<213> ORGANISM: Artificial Sequence
<220> FEATURE:
<223> OTHER INFORMATION: primer for promoter

<400> SEQUENCE: 8
aaggaagaaa aggattga                                                    18

<210> SEQ ID NO 9
<211> LENGTH: 23
<212> TYPE: DNA
<213> ORGANISM: Artificial Sequence
<220> FEATURE:
<223> OTHER INFORMATION: primer for 5'UTR

<400> SEQUENCE: 9
gggagtagga gtaggaggag gaa                                              23

<210> SEQ ID NO 10
<211> LENGTH: 28
<212> TYPE: DNA
<213> ORGANISM: Artificial Sequence
<220> FEATURE:
<223> OTHER INFORMATION: primer for 5' UTR

<400> SEQUENCE: 10
accaaaacaa aaccaaacct cctaccca                                         28

<210> SEQ ID NO 11
<211> LENGTH: 20
<212> TYPE: DNA
<213> ORGANISM: Artificial Sequence
<220> FEATURE:
<223> OTHER INFORMATION: primer for 5' UTR

<400> SEQUENCE: 11
agtaggagta ggaggaggaa                                                  20

<210> SEQ ID NO 12
<211> LENGTH: 24
<212> TYPE: DNA
<213> ORGANISM: Artificial Sequence
<220> FEATURE:
<223> OTHER INFORMATION: primer for 1st intron

<400> SEQUENCE: 12
ygtttttyga gattagggat gatt                                             24

<210> SEQ ID NO 13
<211> LENGTH: 18
<212> TYPE: DNA
<213> ORGANISM: Artificial Sequence
<220> FEATURE:
<223> OTHER INFORMATION: primer for 1st intron

<400> SEQUENCE: 13

```
tctccccaaa acttacat                                                 18

<210> SEQ ID NO 14
<211> LENGTH: 17
<212> TYPE: DNA
<213> ORGANISM: Artificial Sequence
<220> FEATURE:
<223> OTHER INFORMATION: primer for 1st intron

<400> SEQUENCE: 14
gggatgattt ggaaatt                                                  17

<210> SEQ ID NO 15
<211> LENGTH: 25
<212> TYPE: DNA
<213> ORGANISM: Artificial Sequence
<220> FEATURE:
<223> OTHER INFORMATION: primer for SDC2

<400> SEQUENCE: 15
tagaaattaa taagtgagag ggcgt                                         25

<210> SEQ ID NO 16
<211> LENGTH: 22
<212> TYPE: DNA
<213> ORGANISM: Artificial Sequence
<220> FEATURE:
<223> OTHER INFORMATION: primer for SDC2

<400> SEQUENCE: 16
gactcaaact cgaaaactcg aa                                            22

<210> SEQ ID NO 17
<211> LENGTH: 24
<212> TYPE: DNA
<213> ORGANISM: Artificial Sequence
<220> FEATURE:
<223> OTHER INFORMATION: primer for SDC2

<400> SEQUENCE: 17
agtaggcgta ggaggaggaa gcga                                          24

<210> SEQ ID NO 18
<211> LENGTH: 26
<212> TYPE: DNA
<213> ORGANISM: Artificial Sequence
<220> FEATURE:
<223> OTHER INFORMATION: primer for COL2A1

<400> SEQUENCE: 18
gtaatgttag gagtattttg tgggta                                        26

<210> SEQ ID NO 19
<211> LENGTH: 24
<212> TYPE: DNA
<213> ORGANISM: Artificial Sequence
<220> FEATURE:
<223> OTHER INFORMATION: primer for COL2A1

<400> SEQUENCE: 19
ctaccccaaa aaacccaat ccta                                           24

<210> SEQ ID NO 20
<211> LENGTH: 27
<212> TYPE: DNA
<213> ORGANISM: Artificial Sequence
```

<220> FEATURE:
<223> OTHER INFORMATION: probe for COL2A1

<400> SEQUENCE: 20
agaagaaggg aggggtgtta ggagagg                                              27

<210> SEQ ID NO 21
<211> LENGTH: 40
<212> TYPE: DNA
<213> ORGANISM: Artificial Sequence
<220> FEATURE:
<223> OTHER INFORMATION: probe

<400> SEQUENCE: 21
aaaccagaaa ctgaacctcg gcacgggaaa ggagtccgcg                                40

<210> SEQ ID NO 22
<211> LENGTH: 50
<212> TYPE: DNA
<213> ORGANISM: Artificial Sequence
<220> FEATURE:
<223> OTHER INFORMATION: probe

<400> SEQUENCE: 22
gaggagcaaa accacagcag agcaagaaga gcttcagaga gcagccttcc                     50

<210> SEQ ID NO 23
<211> LENGTH: 60
<212> TYPE: DNA
<213> ORGANISM: Artificial Sequence
<220> FEATURE:
<223> OTHER INFORMATION: probe

<400> SEQUENCE: 23
actccgtgtc gggagtgcag aaaccaacaa gtgagagggc gccgcgttcc cggggcgcag          60

<210> SEQ ID NO 24
<211> LENGTH: 60
<212> TYPE: DNA
<213> ORGANISM: Artificial Sequence
<220> FEATURE:
<223> OTHER INFORMATION: probe

<400> SEQUENCE: 24
ctgcgggcgg cgggagcagg cgcaggagga ggaagcgagc gcccccgagc cccgagcccg          60

<210> SEQ ID NO 25
<211> LENGTH: 60
<212> TYPE: DNA
<213> ORGANISM: Artificial Sequence
<220> FEATURE:
<223> OTHER INFORMATION: probe

<400> SEQUENCE: 25
agtccccgag cctgagccgc aatcgctgcg gtactctgct ccggattcgt gtgcgcgggc          60

<210> SEQ ID NO 26
<211> LENGTH: 28
<212> TYPE: DNA
<213> ORGANISM: Artificial Sequence
<220> FEATURE:
<223> OTHER INFORMATION: probe

<400> SEQUENCE: 26
tgtcgtagtt tttttttaag ttagcgaa                                             28

<210> SEQ ID NO 27
<211> LENGTH: 32
<212> TYPE: DNA
<213> ORGANISM: Artificial Sequence
<220> FEATURE:
<223> OTHER INFORMATION: probe

<400> SEQUENCE: 27
aatttcggta cgggaaagga gttcgcggag ga                          32

<210> SEQ ID NO 28
<211> LENGTH: 44
<212> TYPE: DNA
<213> ORGANISM: Artificial Sequence
<220> FEATURE:
<223> OTHER INFORMATION: probe

<400> SEQUENCE: 28 gtttttcgg agtattaatt cgtgtcggg agtgtagaaa ttaa              44

<210> SEQ ID NO 29
<211> LENGTH: 46
<212> TYPE: DNA
<213> ORGANISM: Artificial Sequence
<220> FEATURE:
<223> OTHER INFORMATION: probe

<400> SEQUENCE: 29
gtgagagggc gtcgcgtttt cggggcgtag ttgcgggcgg cgggag           46

<210> SEQ ID NO 30
<211> LENGTH: 47
<212> TYPE: DNA
<213> ORGANISM: Artificial Sequence
<220> FEATURE:
<223> OTHER INFORMATION: probe

<400> SEQUENCE: 30
ggcgtaggag gaggaagcga gcgttttcga gtttcgagtt cgagttt          47

<210> SEQ ID NO 31
<211> LENGTH: 57
<212> TYPE: DNA
<213> ORGANISM: Artificial Sequence
<220> FEATURE:
<223> OTHER INFORMATION: probe

<400> SEQUENCE: 31
tcgagtttga gtcgtaatcg ttgcggtatt tgtttcgga ttcgtgtgcg cgggttg   57

<210> SEQ ID NO 32
<211> LENGTH: 40
<212> TYPE: DNA
<213> ORGANISM: Artificial Sequence
<220> FEATURE:
<223> OTHER INFORMATION: probe

<400> SEQUENCE: 32 tagaaaggg aaagtgaaga agggaaagag aaaagacaac                   40

<210> SEQ ID NO 33
<211> LENGTH: 50
<212> TYPE: DNA
<213> ORGANISM: Artificial Sequence
<220> FEATURE:
<223> OTHER INFORMATION: probe

```
<400> SEQUENCE: 33
ggagagagga aaagtgggga gagaaaggaa gaaaaggact gagaaaacgc                50

<210> SEQ ID NO 34
<211> LENGTH: 60
<212> TYPE: DNA
<213> ORGANISM: Artificial Sequence
<220> FEATURE:
<223> OTHER INFORMATION: probe

<400> SEQUENCE: 34
cggagctgcc aatcggcgtg taatcctgta ggaatttctc ccgggtttat ctgggagtca     60

<210> SEQ ID NO 35
<211> LENGTH: 40
<212> TYPE: DNA
<213> ORGANISM: Artificial Sequence
<220> FEATURE:
<223> OTHER INFORMATION: probe

<400> SEQUENCE: 35
ctgccgtagc tccctttcaa gccagcgaat ttattcctta                          40

<210> SEQ ID NO 36
<211> LENGTH: 50
<212> TYPE: DNA
<213> ORGANISM: Artificial Sequence
<220> FEATURE:
<223> OTHER INFORMATION: probe

<400> SEQUENCE: 36
gcacgggaaa ggagtccgcg gaggagcaaa accacagcag agcaagaaga                50

<210> SEQ ID NO 37
<211> LENGTH: 60
<212> TYPE: DNA
<213> ORGANISM: Artificial Sequence
<220> FEATURE:
<223> OTHER INFORMATION: probe

<400> SEQUENCE: 37
gcagccttcc cggagcacca actccgtgtc gggagtgcag aaaccaacaa gtgagagggc     60

<210> SEQ ID NO 38
<211> LENGTH: 60
<212> TYPE: DNA
<213> ORGANISM: Artificial Sequence
<220> FEATURE:
<223> OTHER INFORMATION: probe

<400> SEQUENCE: 38
gccgcgttcc cggggcgcag ctgcgggcgg cgggagcagg cgcaggagga ggaagcgagc     60

<210> SEQ ID NO 39
<211> LENGTH: 60
<212> TYPE: DNA
<213> ORGANISM: Artificial Sequence
<220> FEATURE:
<223> OTHER INFORMATION: probe

<400> SEQUENCE: 39
gcccccgagc cccagcccg agtccccgag cctgagccgc aatcgctgcg gtactctgct      60

<210> SEQ ID NO 40
```

```
<211> LENGTH: 28
<212> TYPE: DNA
<213> ORGANISM: Artificial Sequence
<220> FEATURE:
<223> OTHER INFORMATION: probe

<400> SEQUENCE: 40
agaaaacgta ggagttttgg tttgtcgg                                        28

<210> SEQ ID NO 41
<211> LENGTH: 32
<212> TYPE: DNA
<213> ORGANISM: Artificial Sequence
<220> FEATURE:
<223> OTHER INFORMATION: probe

<400> SEQUENCE: 41
tagagtcggc gtagttatag cgcggagtcg cg                                   32

<210> SEQ ID NO 42
<211> LENGTH: 36
<212> TYPE: DNA
<213> ORGANISM: Artificial Sequence
<220> FEATURE:
<223> OTHER INFORMATION: probe

<400> SEQUENCE: 42
ttcgggttta tttgggagtt atattgtcgt tttttt                               36

<210> SEQ ID NO 43
<211> LENGTH: 57
<212> TYPE: DNA
<213> ORGANISM: Artificial Sequence
<220> FEATURE:
<223> OTHER INFORMATION: probe

<400> SEQUENCE: 43
gagttcggag aagtaggttt aggagggagg gagttagagg aaaagaagag gaggaga        57

<210> SEQ ID NO 44
<211> LENGTH: 45
<212> TYPE: DNA
<213> ORGANISM: Artificial Sequence
<220> FEATURE:
<223> OTHER INFORMATION: probe

<400> SEQUENCE: 44
cggggaggga ggcgcggcgc gggaggagga ggggcgtagt cgcgg                     45

<210> SEQ ID NO 45
<211> LENGTH: 29
<212> TYPE: DNA
<213> ORGANISM: Artificial Sequence
<220> FEATURE:
<223> OTHER INFORMATION: probe

<400> SEQUENCE: 45
cggatcgcgc gttttcgtcg ttttgtttt                                       29

<210> SEQ ID NO 46
<211> LENGTH: 29
<212> TYPE: DNA
<213> ORGANISM: Artificial Sequence
<220> FEATURE:
<223> OTHER INFORMATION: probe

<400> SEQUENCE: 46
```

```
gaatttcggt acgggaaagg agttcgcgg                                            29
```

<210> SEQ ID NO 47
<211> LENGTH: 24
<212> TYPE: DNA
<213> ORGANISM: Artificial Sequence
<220> FEATURE:
<223> OTHER INFORMATION: primer for SDC2

<400> SEQUENCE: 47

```
gtagaaatta ataagtgaga gggc                                                 24
```

<210> SEQ ID NO 48
<211> LENGTH: 22
<212> TYPE: DNA
<213> ORGANISM: Artificial Sequence
<220> FEATURE:
<223> OTHER INFORMATION: primer for SDC2

<400> SEQUENCE: 48

```
acgactcaaa ctcgaaaact cg                                                   22
```

<210> SEQ ID NO 49
<211> LENGTH: 22
<212> TYPE: DNA
<213> ORGANISM: Artificial Sequence
<220> FEATURE:
<223> OTHER INFORMATION: probe for SDC2

<400> SEQUENCE: 49

```
ttcggggcgt agttgcgggc gg                                                   22
```

<210> SEQ ID NO 50
<211> LENGTH: 24
<212> TYPE: DNA
<213> ORGANISM: Artificial Sequence
<220> FEATURE:
<223> OTHER INFORMATION: primer for COL2A1

<400> SEQUENCE: 50

```
ctaccccaaa aaacccaat ccta                                                  24
```

<210> SEQ ID NO 51
<211> LENGTH: 24
<212> TYPE: DNA
<213> ORGANISM: Artificial Sequence
<220> FEATURE:
<223> OTHER INFORMATION: primer for COL2A1

<400> SEQUENCE: 51

```
ctaccccaaa aaacccaat ccta                                                  24
```

<210> SEQ ID NO 52
<211> LENGTH: 27
<212> TYPE: DNA
<213> ORGANISM: Artificial Sequence
<220> FEATURE:
<223> OTHER INFORMATION: probe for COL2A1

<400> SEQUENCE: 52

```
agaagaaggg aggggtgtta ggagagg                                              27
```

<210> SEQ ID NO 53
<211> LENGTH: 24
<212> TYPE: DNA

```
<213> ORGANISM: Artificial Sequence
<220> FEATURE:
<223> OTHER INFORMATION: primer for SDC2
<220> FEATURE:
<221> NAME/KEY: misc_feature
<222> LOCATION: (21)..(21)
<223> OTHER INFORMATION: n is a, c, g, or t

<400> SEQUENCE: 53
gtagaaatta ataagtgaga nggc                                          24

<210> SEQ ID NO 54
<211> LENGTH: 22
<212> TYPE: DNA
<213> ORGANISM: Artificial Sequence
<220> FEATURE:
<223> OTHER INFORMATION: primer for SDC2
<220> FEATURE:
<221> NAME/KEY: misc_feature
<222> LOCATION: (19)..(19)
<223> OTHER INFORMATION: n is a, c, g, or t

<400> SEQUENCE: 54
acgactcaaa ctcgaaaant cg                                            22

<210> SEQ ID NO 55
<211> LENGTH: 22
<212> TYPE: DNA
<213> ORGANISM: Artificial Sequence
<220> FEATURE:
<223> OTHER INFORMATION: probe for SDC2

<400> SEQUENCE: 55
ttcggggcgt agttgcgggc gg                                            22

<210> SEQ ID NO 56
<211> LENGTH: 26
<212> TYPE: DNA
<213> ORGANISM: Artificial Sequence
<220> FEATURE:
<223> OTHER INFORMATION: primer for COL2A1
<220> FEATURE:
<221> NAME/KEY: misc_feature
<222> LOCATION: (24)..(24)
<223> OTHER INFORMATION: n is a, c, g, or t

<400> SEQUENCE: 56
gtaatgttag gagtattttg tggnta                                        26

<210> SEQ ID NO 57
<211> LENGTH: 24
<212> TYPE: DNA
<213> ORGANISM: Artificial Sequence
<220> FEATURE:
<223> OTHER INFORMATION: primer for COL2A1
<220> FEATURE:
<221> NAME/KEY: misc_feature
<222> LOCATION: (4)..(4)
<223> OTHER INFORMATION: n is a, c, g, or t

<400> SEQUENCE: 57
ctancccaaa aaacccaat ccta                                           24

<210> SEQ ID NO 58
<211> LENGTH: 27
<212> TYPE: DNA
<213> ORGANISM: Artificial Sequence
<220> FEATURE:
<223> OTHER INFORMATION: probe for COL2A1
```

```
<400> SEQUENCE: 58
agaagaaggg aggggtgtta ggagagg                                               27
```